United States Patent
Weidner

(10) Patent No.: US 8,084,049 B2
(45) Date of Patent: Dec. 27, 2011

(54) COMPLEXES OF FATTY ACID ESTERS OF POLYHYDROXYALKANES AND PYRIDINE CARBOXY DERIVATIVES

(75) Inventor: Morten Sloth Weidner, Virum (DK)

(73) Assignee: Astion Dermatology A/S, Copenhagen (DK)

( * ) Notice: Subject to any disclaimer, the term of this patent is extended or adjusted under 35 U.S.C. 154(b) by 690 days.

(21) Appl. No.: 10/517,592

(22) PCT Filed: Jun. 20, 2003

(86) PCT No.: PCT/DK03/00423
§ 371 (c)(1),
(2), (4) Date: Aug. 15, 2005

(87) PCT Pub. No.: WO04/000333
PCT Pub. Date: Dec. 31, 2003

(65) Prior Publication Data
US 2006/0069131 A1 Mar. 30, 2006

Related U.S. Application Data

(60) Provisional application No. 60/389,879, filed on Jun. 20, 2002.

(30) Foreign Application Priority Data

Jun. 20, 2002 (DK) .................................. 2002 00951

(51) Int. Cl.
*A61K 8/02* (2006.01)
*A61K 31/44* (2006.01)
*A61K 31/21* (2006.01)

(52) U.S. Cl. .......................... 424/401; 514/356; 514/506

(58) Field of Classification Search .................. 424/401; 514/356, 406
See application file for complete search history.

(56) References Cited

U.S. PATENT DOCUMENTS

| | | | | |
|---|---|---|---|---|
| 3,676,556 A * | 7/1972 | De Ritter et al. | ............. | 514/355 |
| 4,002,775 A | 1/1977 | Kabara | | |
| 5,231,087 A | 7/1993 | Thornfeldt | | |
| 5,759,584 A * | 6/1998 | Traupe et al. | ................. | 424/520 |
| 6,087,391 A * | 7/2000 | Weidner | ........................ | 514/458 |

FOREIGN PATENT DOCUMENTS

| | | | |
|---|---|---|---|
| EP | 0 465 423 A | | 1/1992 |
| WO | WO 96 34858 A | | 11/1996 |
| WO | WO 0071093 A1 | * | 11/2000 |
| WO | WO 01 03696 A | | 1/2001 |
| WO | WO 01/51051 A2 | | 7/2001 |
| WO | WO 01 74780 A | | 10/2001 |
| WO | WO 01 74781 A | | 10/2001 |
| WO | WO 01/91704 A1 | | 12/2001 |
| WO | WO 02 05850 A | | 1/2002 |
| WO | WO 02 083058 A | | 10/2002 |

OTHER PUBLICATIONS

Shalita et al. "Topical Nicotinamide Compared with Clindamycin Gel in the Treatment of Inflammatory Acne Vulgaris" Int. J. Derm., vol. 4, No. 6, Jun. 1995, pp. 434-437.*
Eady et al., "Antibiotic-resistant propionibacteria in acne: need for policies to modify antibiotic usage" BMJ, 1993; 306: pp. 555-556.*
Cornwell et al., "Glyceryl monocaprylate/caprate as a moderate skin penetration enhancer," International Journal of Pharmaceutics, 171 (1998); pp. 243-255.*
Wu Yuan. "Observation on Therapeutic Effect of Niacinamide Cream in the Treatment of Adolescent Acne," *The Chinese Journal of Dermatovenereology*, May, 1998, vol. 12, No. 3, pp. 1&2.
International Search Report, Date of mailing: Sep. 20, 2004.
McCarty M F et al., "Niacinamide Therapy for Osteoarthritis—Does It Inhibit Nitric Oxide Synthase Induction by Interleukin-1 in Chondrocytes?" Medical Hypotheses, Eden Press, Penrith US vol. 53, No. 4, Oct. 1999, pp. 350-360 XP002901806 ISSN: 0306-9877 Abstract.

* cited by examiner

*Primary Examiner* — Sreeni Padmanabhan
*Assistant Examiner* — Jody Karol
(74) *Attorney, Agent, or Firm* — Stephen A. Bent; Foley & Lardner LLP

(57) ABSTRACT

The present invention relates to novel combinations of fatty acid derivatives and pyridine carboxy derivatives, including fatty acid esters with glycerol and 3-carboxy pyridine derivatives such as niacinamide. Such combinations have surprisingly shown antiviral and anti-microbial activity and the use for the treatment of inflammatory conditions and infections is disclosed herein.

7 Claims, No Drawings

COMPLEXES OF FATTY ACID ESTERS OF POLYHYDROXYALKANES AND PYRIDINE CARBOXY DERIVATIVES

FIELD OF THE INVENTION

The present invention relates to chemical complexes and pharmaceutical compositions comprising a combination of a fatty acid ester of a polyhydroxyalkane and a pyridine carboxy derivative. Their therapeutic application as agents for suppression of hypersensitivity and inflammatory reactions with additional anti-microbial effects, such as bactericidal or fungicidal actions, is disclosed herein.

BACKGROUND OF THE INVENTION

Hypersensitivity is defined as a state of altered reactivity in which the body reacts with an exaggerated immune response to a substance (antigen). Hypersensitivity may be caused by exogenous or endogenous antigens. Hypersensitivity reactions underlie a large number of diseases. Among these, allergic and autoimmune conditions are of great importance. A classification of hypersensitivity diseases is given in the textbook Clinical Medicine (Kumar, P. and Clark, M.: "Clinical Medicine", 3rd edition, p. 147-150, 1994, Bailliere Tindall, London).

Type I hypersensitivity reactions (IgE mediated allergic reactions) are caused by allergens (specific exogenous antigens), e.g. pollen, house dust, animal dandruff, moulds, etc. Allergic diseases in which type I reactions play a significant role include asthma, eczema (atopic dermatitis), urticaria, allergic rhinitis and anaphylaxis.

Type II hypersensitivity reactions are caused by cell surface or tissue bound antibodies (IgG and IgM) and play a significant role in the pathogenesis of myasthenia gravis, Good-pasture's syndrome and Addisonian pernicious anaemia.

Type III hypersensitivity reactions (immune complex) are caused by autoantigens or exogenous antigens, such as certain bacteria, fungi and parasites. Diseases in which type III hypersensitivity reactions play a significant role include lupus erythematosus, rheumatoid arthritis and glomerulonephritis.

Type IV hypersensitivity reactions (delayed) are caused by cell or tissue bound antigens. This type of hypersensitivity plays a significant role in a number of conditions, e.g. graft-versus-host disease, leprosy, contact dermatitis and reactions due to insect bites.

Type I to type IV hypersensitivity reactions are all classically allergic reactions, which may lead to histamine release. However, hypersensitivity reactions are also those, where histamine release is triggered through the directly action of "triggering substances" with the cellular membrane. Examples of "triggering substances" are, but not limited to, toxins, food constituents and certain drugs.

A number of drug classes are available for the treatment of hypersensitivity and related inflammatory reactions.

Among these, the corticosteroids are some of the most widely used drugs. Corticosteroids primarily exert their pharmacological action by non-selectively inhibiting the function and proliferation of different classes of immune cells resulting in suppression of hypersensitivity reactions. Unfortunately, the corticosteroids are associated with a number of serious side effects, e.g. immunosuppression, osteoporosis and skin atrophy. Alternative drugs are associated with serious toxicity. There is a strong need for effective and safer alternatives to the existing antiinflammatory drugs.

Often hypersensitivity or inflammatory disease as described above is associated with or even caused by pathogenic bacteria, fungi or viruses. A number of pathogenic bacteria and fungi play an essential role in the development of a plethora of diseases, including skin diseases. For example, atopic dermatitis, which is widely considered as an inflammatory skin disorder is often associated with secondary infections, e.g. with *Staphylococcus Aureus*, thus giving rise to aggravation of the symptoms. Similarly, the facial eczematous disease seborrheic dermatitis is associated with fungal infections, typically caused by *Pityrosporum ovale*. Today, such skin diseases are often treated with corticosteroids. Antibiotics may also be applied, but today the topical application of traditional antibiotics is limited due to the risk of adverse effects and development of resistant strains of micro organisms, which can cause severe problems.

Herpes labialis (cold sores) is associated primarily with unpleasant inflammation and blisters occurring on the lips and face as the primary symptoms, but the cause of the disease is a viral infection with Herpes simplex type 1.

Similarly, acne vulgaris is an inflammatory disease of the sebaceous glands and hair follicles of the skin, but a primary cause of the disease is a bacterial infection with *Propionibacterium acnes*.

Infections are treated with antibiotics with diverse specific mechanisms of action and often associated with unpleasant adverse effects. Unfortunately antibiotics often give rise to the development of resistance. Resistant strains of bacteria, which are practically untreatable, are a growing problem due to the widespread use of antibiotics.

Obviously there is a strong need for safer antibiotics and treatments that combine antibacterial, antiviral or antifungal effects with symptom relieving antiinflammatory effects.

Niacinamide, which is also known as nicotinamide, has been found to be a potent inhibitor of poly(ADP-ribose)polymerase.

Poly(ADP-ribose)polymerase, also known as poly(ADP-ribose)synthetase or poly(ADP-ribose)transferase is an nuclear enzyme that catalyses the posttranslational modification of nuclear proteins by covalent attachment of ADP-ribosyl moieties derived from $NAD^+$ with an accompanying release of nicotinic acid amide. Preferred acceptor proteins are nuclear histones, whose poly-ADP-ribosylation induces local alterations in the architecture of chromatin domains.

Inhibitors of poly(ADP-ribose)polymerase have been found to suppress hypersensitivity reactions and inflammation. Thus, Ungerstedt et al. (Clin Exp Immunol. 2003 January; 131(1):48-52) found that niacinamide inhibits the expression in human whole blood of the pro-inflammatory cytokines IL-1β, IL-6, IL-8 and TNF-α. This may explain some of the beneficial effects reported, e.g. in the prophylaxis of aggravation of diabetes and symptoms of osteoarthritis as elaborated by McCarthy et al (Med Hypotheses. 1999 October; 53(4):350-60). Still niacinamide and similar pyridine carboxy derivatives are considered as mild and speculative antiinflammatory agents, which is also why they are not at present in established clinical use.

JP 964497 discloses the use of niacinamide for preventing mildew and for use as a food preservative. There is no mention of medicinal use or use as an antibiotic.

Disinfecting properties of fatty acids have been acknowledged for more than a century. The use of bar soap is a practical example of this, which besides solubilization of dirt also provides a mild degree of disinfection of the skin. The acknowledgement of the preferable use of certain fatty acids or derivatives thereof for inhibition of microorganisms is exemplified by U.S. Pat. No. 4,002,775, which discloses the use of specific fatty acids and derivatives as antimicrobial agents in relation to food preservation.

EP 465423 discloses a pharmaceutical composition for killing microorganisms containing fatty acids and monoglycerides thereof. Fatty acid esters of other glycols are not disclosed and the combination or complex formation with pyridine carboxy derivatives is not mentioned. Therefore the relevance to the present invention is limited.

The same is the case with WO 9820872, which discloses a method for counteracting infection of the genital mucosa of a mammal by applying compositions containing $C_6$ to $C_{18}$ fatty acids or monoglycerides or fatty alcohol esters thereof to the genital mucosa.

U.S. Pat. No. 5,231,087 discloses a method of treating certain skin diseases and tumours with esters and amides of monocarboxylic acids having 9 to 18 carbon atoms. The proposed esters include esters of a broad variety of alcohols ranging from monohydric alcohols up to esters of saccharides and polyethylene glycol, which is completely besides the scope of the present invention. Furthermore there is no disclosure of combination or complex formation with pyridine carboxy derivatives.

As recognised by the present inventor, there is a need for agents that provide combined anti-inflammatory and antimicrobial therapeutic effects in an efficient manner and without the adverse effects associated with existing medication.

SUMMARY OF THE INVENTION

The present inventor has found that a combination of a fatty acid ester of a polyhydroxyalkane and a pyridine carboxy derivative significantly suppresses inflammatory reactions. Both of these groups of components of the complexes of the invention hold the advantage of being non-toxic and very well tolerated compared to existing antiinflammatory drugs, which are generally associated with severe and treatment limiting adverse effects. Experimental data presented in example 111 demonstrate that the surprising and powerful antiinflammatory effects of the complexes of the invention are due to a synergistic effect between the components of the complexes of the invention. At the dose giving maximal effect in a recognised mouse model of dermal inflammation the complex of the invention gave 65% more inhibition of inflammation than the sum of the effect of the same amount of the components when administered alone. This clear synergistic effect made it possible for this combination of two safe and non-toxic substances to give exactly the same antiinflammatory effect as betamethasone 17-valerate, one of the strongest topical steroids used to treat skin diseases, which may only be used for a few weeks at a time due to significant damaging effects on the skin, including atrophy and unhealable wounds. Today no safe alternatives exist for such products and the complexes of the invention may revolutionise the treatment of chronic inflammatory diseases. In another animal study (example 112) simulating chronic inflammatory skin disease, which is particularly difficult to treat, another complex according to the invention was tested against betamethasone 17-valerate. In this pharmacological model mild steroids like hydrocortisone have no measurable effects. All three doses of the complex of the invention gave a statistically significant and dose dependent inhibition of inflammation and in the highest dose, which can realistically safely be used in humans, the complex gave a 60% higher inhibition of dermal inflammation than betamethasone 17-valerate (p=0.0089, Mann-Whitney U test). In this study both substances were administered in the maximum dose that can realistically be administered to humans, with the main difference that in the case of the complex of the invention, no toxic or adverse reactions can be anticipated, simply because the components of the complexes are biological molecules compatible with the human organism. Accordingly, the combination of a fatty acid ester of a polyhydroxyalkane and a pyridine carboxy derivative are of use generally in the immunomodulation of a mammal, such as a human. Furthermore, such combinations of components possess broad-spectrum antibacterial and fungicidal properties, thereby making them highly relevant for the treatment of a great number of infectious diseases and inflammatory skin diseases, including those diseases associated with secondary infections, which is a common problem with chronic inflammatory disease. The present inventor provides data herein demonstrating synergistic effects also in relation to antimicrobial effects. As demonstrated in example 113 a minimum inhibitory concentration (MIC) could be established against 5 organisms for the complex, while the individual components at the levels present in the complex could not demonstrate any measurable effect. Interestingly, the specific complex in question was able to significantly suppress a multi-resistant bacterium (mithycillin resistant Staphylococcus aureus).

Contrarily to existing therapeutic agents, such as corticosteroids or non-steroidal anti-inflammatory drugs, the chemical complexes and pharmaceutical compositions according to the present invention have the advantage of not being likely to be associated with any serious side effects, as all of their components are non-toxic and well tolerated by the organism in the pharmacologically relevant doses.

Accordingly, the present invention provides a chemical complex or a pharmaceutical composition comprising:

i) i) a fatty acid ester of formula I or isomers thereof,

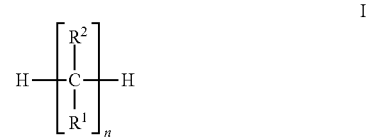

wherein n is 1, 2, 3, 4, 5 or 6;

each $R^1$ and $R^2$ is independently selected from the group consisting of H, OH, OM, OR', O—CO—R', optionally substituted straight-chain or branched $C_1$-$C_6$ alkyl and optionally substituted straight-chain or branched $C_2$-$C_6$ alkenyl, wherein R' is selected from the group consisting of optionally substituted $C_6$-$C_{20}$ alkyl and optionally substituted $C_6$-$C_{20}$ alkenyl, and wherein M is an alkali metal;

provided that at least one of $R^1$ and $R^2$ is a group —O—CO—R' or —OR'; and ii) a pyridine derivative of formula II or a salt thereof,

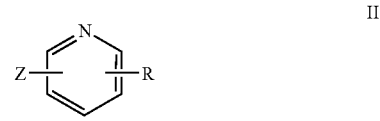

wherein R is one substituent selected from the group consisting of —C(=X)$R_a$" and —CH($R_b$")XH;

wherein X is O or S, $R_a$" is selected from the group consisting of H, OH, OR''', $NH_2$, NHR''', NR'''R'''', $CH_2COOH$, $O^-Y^+$ and halogen, R$_b$" is selected from the group consisting of H and CH$_2$COOH, wherein R'" and R"" are independently selected from H, OH, optionally substituted C$_1$-C$_{20}$ straight-chain, branched or cyclic alkyl, optionally containing one or more multiple bonds, and aryl, and wherein Y$^+$ is a cation selected from optionally substituted mono-, di-, tri- or tetraalkylammonium ions, ammonium ion, and alkali metal ions;

Z is present 0, 1, 2, 3, or 4 times and selected from the group consisting of hydrogen, halogen, NH$_2$, methyl, OR'" or —SH.

The chemical complexes and pharmaceutical compositions according to the invention may be employed for therapeutic applications such as i) immunomodulation, ii) the treatment of hypersensitivity diseases; iii) the treatment of inflammatory diseases, iv) the treatment of IgE mediated allergic reactions and conditions; v) the treatment of autoimmune disorders; vi) the alleviation of pain; vii) the treatment of infectious diseases, e.g. bacterial, viral, or fungal infections and viii) the treatment inflammation associated with cancer.

An important aspect of the invention relates to the use of a combination of a fatty acid ester of a polyhydroxyalkane and a pyridine carboxy derivative for the preparation of a product for the treatment of infections or diseases associated with infections selected from the group consisting of microbial infections, viral infections, infections caused by parasites, infections caused by fungi in a mammal, such as a human, as well as to a method for the treatment of infections or diseases associated with infections selected from the group consisting of microbial infections, viral infections, infections caused by parasites, infections caused by fungi in a mammal, such as a human, comprising the administration of an effective amount of a combination of a fatty acid ester of a polyhydroxyalkane and a pyridine carboxy derivative, or a complex comprising said combination to said mammal.

Of particular interest is the treatment of viral and microbial infections or diseases associated with infections caused by virus or a bacterie.

Still further aspects relate to anti-hypersensitivity and anti-inflammatory activity of said combination of a fatty acid ester and a pyridine carboxy derivative, for which reason said invention also relate to a method for the suppression of hypersensitivity and/or inflammatory reaction in a mammal, such as the treatment of a disease and disorder associated with hypersensitivity and/or inflammatory reactions. Included herein is the treatment of hypersensitivity and/or inflammatory skin diseases in general and in particularly with respect to the treatment of pruritus, urticaria, of atopic eczema, contact dermatitis, seborrhoeic dermatitis, acne, rosacea, alopecia, vitiligo and/or psoriasis.

In still further aspects, the treatment of a hypersensitivity and/or an inflammatory conditions relates to the treatment of IgE mediated allergic reaction in general and particularly with respect to asthma, allergic rhinitis, and/or anaphylaxis; a method for the treatment of autoimmune disease and/or chronic inflammatory disease in general and particularly with respect to diabetes, Crohn's disease, ulcerative colitis, rheumatoid arthritis, gout or osteoarthritis; a method for the treatment of cancer; and to a method for the alleviation of pain; each method comprising the administration of an effective amount of a combination of a fatty acid ester of a polyhydroxyalkane and a pyridine carboxy derivative, or a complex or composition comprising said combination to a mammal, such as a human.

In still further aspects, the combination of a fatty acid ester and a pyridine carboxy derivative as disclosed herein is for use as a dietary supplement or a cosmetic, such as for example for the cosmetic treatment of conditions selected from the group consisting of acne, acne prone skin, irritated skin, dry skin, skin redness, scaly or flaking skin, sunburn or as an antiseptic agent, disinfectant, bacteriostatic agent, bactericidal agent, protective agent, and/or regenerating agent.

DETAILED DESCRIPTION OF THE INVENTION

The present inventor provides data herein indicating that a combination of a fatty acid ester of polyhydroxyalkanes synergistically reduces the inflammation in a well-established in vivo test models of both acute and chronic inflammation. The reduction of inflammation was comparable to or even superior to one of the strongest topical steroids in clinical use at therapeutically relevant doses of betamethasone 17-valerate. Consequently, the combination of fatty acid esters of polyhydroxyalkanes and pyridine carboxy derivate is unexpectedly effective in suppressing hypersensitivity and inflammatory reactions. Moreover, surprisingly, the present combinations according to the invention were proved to be effective in inhibiting the growth of a number of microorganisms, including *Candida Albicans, Epidermophyton floccosum, Microsporum canis, Streptococcus faecalis* and *Trichophyton rubrum*. However, each of the individual tested components of the complex did not inhibit growth, for which reason the present combination of fatty acid esters of polyhydroxyalkanes and pyridine carboxy derivate seems to have a synergistic effect also with respect to suppression of microbial growth. Also very surprisingly, the present inventor found that combinations according to the invention inhibited the growth of resistant *Staphylococcus Aureus*.

Hence, the combination of a fatty acid ester of a polyhydroxyalkane and a pyridine carboxy derivative significantly suppresses hypersensitivity reactions and/or inflammatory reactions. Such chemical complexes are novel and provide a surprisingly good anti-hypersensitivity and anti-inflammatory effect with a surprisingly good safety profile. Simultaneously, the complexes of the invention provide strong antimicrobial effects, especially in topical application, with a surprisingly broad spectrum of activity against pathogenic bacteria and fungi and with a surprisingly low toxicity for humans providing an excellent safety profile. Thus the chemical complexes or compositions of the invention are virtually non-toxic and yet very therapeutically effective.

According to the invention, said combination of a fatty acid ester of a polyhydroxyalkane and a pyridine carboxy derivative may be provided in the form of a chemical complex. Without being limited to a particular theory, the combination is advantageous provided as a chemical complex for purposes of achieving homogeneous mixtures of the two agents, thereby positively affecting the resulting therapeutic effect. Furthermore, said combination of a fatty acid ester of a polyhydroxyalkane and a pyridine carboxy derivative may be provided as a pharmaceutical composition, dietary supplement or a cosmetic, wherein said combination may be in a chemical complex form or just mixtures of the two individual agents. In some embodiments thereof, said combination of a fatty acid ester of a polyhydroxyalkane and a pyridine carboxy derivative may each be provided in separate compositions.

Such combinations of fatty acid ester of a polyhydroxyalkane and a pyridine carboxy derivative as well as compositions and chemical complexes of said combination are novel and provide a surprisingly effective anti-hypersensitivity and anti-inflammatory effect with a surprisingly good safety profile. Thus the chemical complexes or compositions of the invention are virtually non-toxic and yet very therapeutically effective.

The present inventor proposes the hypothesis that the very advantageous therapeutic index of the combination of a fatty acid ester of a polyhydroxyalkane and a pyridine carboxy derivative in comparison to the individual anti-hypersensitivity or antimicrobial drugs is due to any synergistics effect or complementary effects between the components of the combinations. Thus, this results in a lower toxic load on the body in comparison to any single chemical compound, while still achieving a surprisingly good therapeutic effect.

The invention is based, at least in part, on the synergistic between the pyridine carboxy derivative and the fatty acid ester of a polyhydroxyalkane in comparison to either component. This surprising synergism allows for the combining of any fatty acid ester of a polyhydroxyalkane with an optionally substituted pyridine carboxy derivative to achieve the desired effect at much lower doses than ever anticipated. Moreover, the synergism allows for the use of a fatty acid ester of a polyhydroxyalkane or a pyridine carboxy derivative previously not used for the desired effect due to the high doses required to achieve said effect. Still further, this synergism allows for the use of compounds, which are not used due to the toxicity associated with therapeutically effective doses.

The present invention provides a chemical complex or a pharmaceutical composition comprising:

i) a fatty acid ester of formula I or isomers thereof,

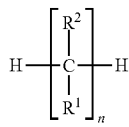

I wherein n is 1, 2, 3, 4, 5 or 6;
each $R^1$ and $R^2$ is independently selected from the group consisting of H, OH, OM, OR', O—CO—R', optionally substituted straight-chain or branched $C_1$-$C_6$ alkyl and optionally substituted straight-chain or branched $C_2$-$C_6$ alkenyl,
wherein R' is selected from the group consisting of optionally substituted $C_6$-$C_{20}$ alkyl and optionally substituted $C_6$-$C_{20}$ alkenyl, and wherein M is an alkali metal;
provided that at least one of $R^1$ and $R^2$ is a group —O—CO—R' or —OR'; and ii) a pyridine derivative of formula II or a salt thereof,

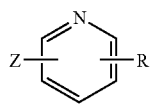

II wherein R is one substituent selected from the group consisting of —C(=X)$R_a$" and —CH($R_b$")XH;
wherein X is O or S,
$R_a$" is selected from the group consisting of H, OH, OR''', $NH_2$, NHR''', NR'''R'''', $CH_2COOH$, $O^-Y^+$ and halogen,
$R_b$" is selected from the group consisting of H and $CH_2COOH$,
wherein R''' and R'''' are independently selected from H, OH, optionally substituted $C_1$-$C_{20}$ straight-chain, branched or cyclic alkyl, optionally containing one or more multiple bonds, and aryl, and wherein $Y^+$ is a cation selected from optionally substituted mono-, di-, tri- or tetraalkylammonium ions, ammonium ion, and alkali metal ions;
Z is present 0, 1, 2, 3, or 4 times and selected from the group consisting of hydrogen, halogen, $NH_2$, methyl, OR''' or —SH.

The term "chemical complex" is intended to include the definition defined by IUPAC that read as follows:

"A molecular entity formed by loose association involving two or more component molecular entities (ionic or uncharged), or the corresponding chemical species. The bonding between the components is normally weaker than in a covalent bond." (IUPAC Compendium of Chemical Terminology 2nd Edition (1997))

Thus, the term "chemical complex" is intended to mean any combination of the component molecules in the context of the IUPAC definition. It is not intended to implye an ionic association or covalent association between the components. Also as used herein, the chemical complex of the present invention relates to a complex obtainable from the combining of a pyridine carboxy derivative of Formula II and a fatty acid ester of a polyhydroxy alkane of Formula I.

The practical and technical implementation of the IUPAC chemical complex definition is that the product is homogeneous at the molecular level and does not for example consist of microphases. An appropriate method for studying a chemical complex will vary from complex to complex but typical methods are x-ray diffraction, differential scanning calorimetry and electron microscopy.

As mentioned, the pyridine carboxy derivative may optionally be substituted. The term "optionally substituted" is intended to mean the substitution of one or more hydrogen atoms is substituted with another atom, chemical group or entity, termed substituents. Illustrative examples of substituents include carboxyl, formyl, amino, hydroxyl, halogen, nitro, sulphono, sulphanyl, C1-6-alkyl, aryl, aryloxy, aryloxycarbonyl, arylcarbonyl, heteroaryl, amino, mono- and di(C1-6-alkyl)amino; carbamoyl, mono- and di(C1-6-alkyl)aminocarbonyl, amino-C1-6-alkyl-aminocarbonyl, mono- and di(C1-6-alkyl)amino-C1-6-alkyl-aminocarbonyl, C1-6-alkylcarbonylamino, cyano, guanidino, carbamido, C1-6-alkanoyloxy, C1-6-alkylsulphonyloxy, dihalogen-C1-6-alkyl, trihalogen-C1-6-alkyl, C1-6-alkoxyl, oxo, C1-6-carboxyl, C1-6-alkoxycarbonyl, C1-6-alkylcarbonyl, where aryl and heteroaryl representing substituents may be substituted 1-5 times with C1-6-alkyl, C1-6-alkoxy, nitro, cyano, hydroxy, amino or halogen. In general, the above substituents may be susceptible to further optional substitution.

The term "$C_1$-$C_{20}$ alkyl" is intended to mean a linear or branched saturated hydrocarbon chain wherein the longest chains has from one to twenty carbon atoms, such as methyl, ethyl, n-propyl, isopropyl, n-butyl, isobutyl, sec-butyl, tert-butyl, pentyl, isopentyl, neopentyl, hexyl, heptyl, octyl, undecacyl, dodecyl, etc. A branched hydrocarbon chain is intended to mean a $C_1$-$C_{20}$ alkyl substituted at any carbon with a hydrocarbon chain. The $C_1$-$C_{20}$ alkyl chain of the present invention may be optionally substituted.

The term "C2-$C_{20}$ alkenyl" is intended to mean a linear or branched unsaturated hydrocarbon chain with one or more double bindings and wherein the longest chains has from one to twenty carbon atoms. A branched hydrocarbon chain is intended to mean a $C_1$-$C_{20}$ alkyl substituted at any carbon with a hydrocarbon chain. The $C_2$-$C_{20}$ alkenyl chain of the present invention may be optionally substituted.

The term "$C_1$-$C_{20}$ alkoxyl" is intended to mean a linear or branched hydrocarbon chain wherein the longest chains has from one to twenty carbon atoms, such as methoxy, ethoxyl, n-propoxyl, isopropoxyl, n-butoxyl, isobutoxyl, isopentoxyl, hexoxyl, heptoxyl, octoxyl, etc. A branched hydrocarbon chain is intended to mean a $C_1$-$C_{20}$ alkyl substituted at any carbon with a hydrocarbon chain. The $C_1$-$C_{20}$ alkyl chain of the present invention may be optionally substituted.

The term "halogen" includes fluorine, chlorine, bromine and iodine.

Concerning the fatty acid derivative of the invention, it is to be Understood that suitable embodiments include those wherein at least one of $R_1$, $R_2$ and $R_3$ is OH. Furthermore, still interesting embodiments include those wherein at most two of $R_1$, $R_2$ and $R_3$ is O—CO—R', preferably one such group. Thus, mono and di-esters of fatty acids and a polyhydroxyalkane are anticipated. In some embodiments thereof, two different fatty acids may be esterified to the polyhydroxyalkane and in other embodiments the fatty acids are identical.

Furthermore, it is to be understood that the ester group, O—CO—R', may be replaced by a ether group, —OR'. Thus, in a further aspect of the invention, the compositions or chemical complexes of the invention comprises an alkylether of a polyhydroxyalkane.

As stated, the esters according to formula I comprise at least one ester group, O—CO—R', wherein R' is an alkyl or an alkenyl with a carbon chain length of at most 20 carbon atoms. However, in suitable embodiments of the invention, the R' are shorter than twenty carbon atoms or longer than one or two carbon atoms. Thus, in various separate embodiments R' is selected from $C_3$-$C_{18}$ alkyl and $C_3$-$C_{18}$ alkenyl; $C_4$-$C_{16}$ alkyl and $C_4$-$C_{16}$ alkenyl; $C_4$-$C_{16}$ alkyl and $C_4$-$C_{16}$ alkenyl; $C_4$-$C_{16}$ alkyl and $C_4$-$C_{16}$ alkenyl; $C_6$-$C_{12}$ alkyl and $C_6$-$C_{12}$ alkenyl; $C_6$-$C_{10}$ alkyl and $C_6$-$C_{10}$ alkenyl; $C_2$-$C_{10}$ alkyl and $C_2$-$C_{10}$ alkenyl; and $C_4$-$C_{10}$ alkyl and $C_4$-$C_{10}$ alkenyl.

As mentioned, each $R^1$ and $R^2$ may independently be selected from the group consisting of H, OH, OM, OR', O—CO—R', optionally substituted straight-chain or branched $C_1$-$C_6$ alkyl and optionally substituted straight-chain or branched $C_2$-$C_6$ alkenyl, wherein M is an alkali metal, such as sodium, potassium or ammonium.

In some suitable embodiments, the group, O—CO—R' is an acyloxy moiety derived from an acid, HO—CO—R', that may be selected from the group consisting of caproic acid, caprylic acid, capric acid, lauric acid, myristic acid, myristoleic acid, palmitic acid, palmitoleic acid, linoleic acid, α-linolenic acid, γ-linolenic acid and ricinoleic acid.

Furthermore, the O—CO—R' may be an acyloxy moiety derived from an acid, HO—CO—R', selected from the group consisting of all-cis-5,8,11,14,17-eicosapentaenoic acid and docosahexaenoic acids (DHA).

As stated, the fatty acid ester is connected with an polyhydroxyalkane of various carbon length such that wherein n is 1, 2, 3, 4, 5 or 6. Preferably, n may be 1, 2 or 3. Typical examples of polyhydroxyalkanes of interest include propylene glycol, glycerol, 1,3-butylene glycol, 2,3-butylene glycol or sorbitol.

The fatty acid ester of a polyhydroxyalkane, for illustrative purposes, may be selected from the group consisting of Ethyleneglycyl-1-hexanoate, Ethyleneglycyl-1-(4-noneoate), Glyceryl-2-(5-ethyl-octanoate), Trimetylenglycyl-1-dodecanoate-2-dodecanoate, Trimetylenglycyl-1-octadecanoate-2-(5,7,9-heptadecatrienoate), 1,2,3,4-butantetraol-1-undecanoate-3-nonanoate, 1-ol-2,3-butylenglycyl-1-heptandecanoate-2-heptandecanoate, Propylenglycyl-2-(3-metyl-decanoate), 1,2-butylenglycyl-1-hexanoate-2-hexanoate, Ethyleneglycyl-1-octanoate, Ethylenglycyl-1-octanoate-4-(3-ethyl-hexanoate), 1,2,3,4-butantetraol-1-hexadecanoate-(4-(2,4-diethyl-8-hexadecenoate), 1,2,3,4-butanetetraol-2-eicosatrienoate, Glyceryl-1-decanoate-2-decanoate, 1,4-butylenglycyl-1-octanoate, 1-ol-2,3-butylenglycyl-1-heptandecanoate-2-heptandecanoate, Propylenglycyl-1-undecanoate-2-undecanoate, Propylenglycyl-1-(7,10-octadecadienoate)-2-octanoate, Glyceryl-2-(8,11,14-eicosatrienoate), Ethylenglycyl-1-decanoate-2-hexanoate, Ethylenglycyl-1-(4-tetradecenoate), Glyceryl-1-octanoate-3-undecanoate, Glyceryl-1-(4-nonenoate)-3-hexanoate, Trimetylglycyl-1-octanoate, Trimetylenglycyl-1-undecanoate, Propylenglycyl-1-hexanoate, Propylenglycyl-2-(3-metyl-decanoate), 1,2-butylenglycyl-2-octanoate, 1,2-butylenglycyl-1-nonaoate-2-octanoate, 1,3-butylenglycyl-1-decanoate-3-octanoate, 2,3-butylenglycyl-2-dodecanoate, 2,3-butylenglycyl-2-octanoate-3-octanoate, Ethylenglycyl-1-(3,6-octadecadienoate)-2-octanoate, Ethylenglycyl-1-(8-metyl-3,6-octadecadienoate), Glyceryl-1-(4,6,10-eicosatrienoate)-2-(4,6,10-eicosatrienoate), Glyceryl-1-(8-octadecenoate)-3-heptanoate, Trimetylenglycyl-2-(4-metyl-2,8-eicosadienoate), Propylenglycyl-1-nonanoate, 1,2,3,4-butantetraol-1-decanoate, 1,2,3,4-butantetraol-1-hexadecanoate-(4-(2,4-diethyl-8-hexadecenoate), 1,2,3,4-butanetetraol-2-eicosatrienoate, 2,3-butylenglycyl-2-hexanoate, 1-ol-2,3-butylenglycyl-1-(4-metyl-hexanoate), 1-ol-2,3-butylenglycyl-1-(3-octenoate), 1,4-butylenglycyl-1-dodecanoate, 1,4-butylenglycyl-1-decanoate-4-decanoate, 1,2,3,4-butantetraol-2-(2-metyl-octanoate), 1,2,3,4-butantetraol-1-hexanoate-2-hexanoate, Glyceryl-2-(3,5,7-hexadecatrienoate), Glyceryl-1-octanoate, Glyceryl-2-octanoate, Glyceryl-2-octanoate, Glyceryl-1-octanoate-2-octanoate, Glyceryl-2-(3,5,7-hexadecatrienoate), Glyceryl-1-(3-ethyl-2-metyl-8,10-eicosadienoate)-2-octanoate, Propylenglycyl-1-(2,4-ethyl-6-tetradecaenoate)-2-(8,12-hexadecaenoate), 1,2-butylenglycyl-1-decanoate, 1,2-butylenglycyl-1-heptadecanoate-2-(4,8-heptadecadienoate), 1,2-butylenglycyl-1-(8-ethyl-4-metyl-6,16-octadecadienoate), Glyceryl-1-(5,8,11,14,17-eicosapentaenoate), Propylenglycyl-1-nonanoate-2-decanoate, Trimetylenglycyl-1-octanoate-2-(4-ethyl-decanoate), 1,3-butylenglycyl-1-undecanoate, 1,3-butylenglycyl-3-hexanoate, 1,3-butylenglycyl-1-octanoate-3-octanoate, 1-ol-2,3-butylenglycyl-1-undecanoate-2-undecanoate, 1-ol-2,3-butylenglycyl-1-(2-ethyl-nonanoate)-2-hexanoate, Glyceryl-2-octanoate, Glyceryl-1-octanoate-2-octanoate, 1,4-butylenglycyl-1-octanoate-4-heptanoate, 2,3-butylenglycyl-2-dodecanoate-3-heptanoate, 1,2,3,4-butantetraol-2-(2-metyl-octanoate), 1,2,3,4-butantetraol-1-hexanoate-2-hexanoate, 1,4-butylenglycyl-1-(6,10,12,18-tetradecantetraenoate)-4-(4,8-dimetyl-6,13-eicosadienoate), 1,4-butylenglycyl-1-(2-ethyl-octanoate)-4-(4-nonenoate), Glyceryl-1-octanoate, Glyceryl-1-(5,8,11,14,17-eicosapentaenoate), Glyceryl-2-(8,11,14-eicosatrienoate), 1,2,3,4-butantetraol-2-(2-metyl-octanoate), Ethyleneglycyl-1-octanoate, Ethylenglycyl-1-octanoate-4-(3-ethyl-hexanoate), Glyceryl-1-octanoate, Glyceryl-1-(5,8,11,14,17-eicosapentaenoate), Glyceryl-2-(8,11,14-eicosatrienoate), Glyceryl-2-(8,11,14-eicosatrienoate), 1,2,3,4-butantetraol-2-(2-metyl-octanoate), Glyceryl-1-octanoate, Trimetylenglycyl-2-(4-metyl-2,8-eicosadienoate), Propylenglycyl-1-nonanoate, Glyceryl-1-(5,8,11,14,17-eicosapentaenoate), Propylenglycyl-1-(2,4-ethyl-6-tetradecaenoate)-2-(8,12-hexadecaenoate), 1,2-butylenglycyl-1-decanoate, 1,2-butylenglycyl-2-octanoate, Glyceryl-2-octanoate, 1,4-butylenglycyl-1-decanoate-4-decanoate, Glyceryl-2-octanoate, Ethylenglycyl-1-decanoate-2-hexanoate, 1-ol-2,3-butylenglycyl-1-(2-ethyl-nonanoate)-2-hexanoate, Glyceryl-2-(8,11,14-eicosatrienoate), derivatives and salts thereof.

In currently preferred embodiments of the invention, the fatty acid ester of the invention is racemic, enantiomerically enriched or enantionerically pure 1-glyceryl-monocaprylate and niacinamide, preferably when provided in a molar ratio 2:7 or 1:14.

As used herein, the pyridine carboxy derivative includes salts of compounds of formula II. The salts may be any pharmaceutically acceptable salt including hydrates, solvent addition forms, acid addition salts. In different embodiments of the invention, the salt is a hydroiodide, hydrochloride or a hydrobromide, e.g. nicotinamide hydroiodide.

The term "base addition salts" include alkali metals, such as sodium and potassium, alkali earth metals, such as calcium and magnesium, and organic addition salts such as quaternary ammonium cations.

As stated, the complex comprises, in part, the optionally substituted pyridine carboxy derivative according to Formula II wherein R is one substituent selected from the group consisting of —C(=X)$R_a$" and —CH($R_b$")XH, wherein X is O or S and $R_a$" is selected from the group consisting of H, OH, OR''', $NH_2$, NHR''', NR'''R'''', $CH_2COOH$, $O^-Y^+$ and halogen. $R_b$" is selected from the group consisting of H and $CH_2COOH$. R''' and R'''' may independently be selected from H, OH, optionally substituted $C_1$-$C_{20}$ straight-chain, branched or cyclic alkyl, optionally containing one or more multiple bonds, and aryl. Thus, R''' and R'''' may independently be selected from optionally substituted C1-C20 alkyl, optionally substituted $C_1$-$C_{20}$ alkoxyl and optionally substituted $C_2$-$C_{20}$ alkenyl. In suitable embodiments, the carbon chain length of R''' and R'''' are shorter than twenty carbon atoms, e.g. from $C_1$-$C_{10}$, $C_1$-$C_8$, $C_1$-$C_6$, $C_1$-$C_4$ or $C_1$-$C_3$ With respect to the optionally substituted alkenyls, the carbon chain length is at least two carbon and may comprise one or more double bonds such as 1, 2, or 3 double bonds. Thus, the optionally substituted alkenyls can have any length, e.g. from $C_2$-$C_{12}$ $C_2$-$C_{10}$, $C_2$-$C_8$, $C_2$-$C_6$, $C_2$-$C_4$ or $C_2$-$C_3$. In suitable embodiments R''' and R'''' may independently be selected from the group consisting of optionally substituted $C_1$-$C_{10}$ alkyl and optionally substituted $C_2$-$C_{10}$ alkenyl and $R_a$" may be OR''', NH2, NHR''' or NR'''R'''' wherein R''' and R'''' may be independently selected from the group consisting of optionally substituted $C_1$-$C_6$ alkyl and optionally substituted $C_2$-$C_6$ alkenyl. Also R''' may be selected from optionally substituted $C_1$-$C_4$ alkyl and optionally substituted $C_1$-$C_4$ alkenyl.

Furthermore, the pyridine carboxy derivative may be subjected to repeatedly ring substitution, such that Z is present 0, 1, 2, 3, or 4 times and selected from the group consisting of hydrogen, halogen, $NH_2$, methyl, OR''' or —SH. Preferably, Z is 0 or 1.

In still further interesting embodiments, the pyridine derivative is a pyridine-3-carboxy derivative, i. e. R is located at the 3-position.

The optionally substituted pyridine carboxy derivative may, for illustrative purposes, be selected from the group consisting of optionally substituted nicotinic acid, its corresponding acyl halide, ester, acid salt, or amide, nicotinamide; optionally substituted isonicotinic acid, its corresponding acyl halide, ester, acid salt, or amide, isonicotinamide; and optionally substituted picolinic acid, its corresponding acyl halide, ester, acid salt, or amide, picolinamide.

In very interesting embodiments of the invention, the pyridine carboxy derivative is pyridine-3-carboxy derivative. Hence, in different embodiments of the invention, the pyridine carboxy derivative is selected from the group consisting of niacinamide, thioniacinamide, 6-aminoniacinamide, $N^2$-methylniacinamide, $N^2$-ethylniacinamide, nicotinic acid, 6-methoxy-niacinamide and salts thereof. Moreover, it is also anticipated that polymeric forms of nicotinic acid may be applicable. Thus, in one embodiment the pyridine derivative is inosital hexaniacinate which can be viewed as a prodrug. Moreover, quinolinic acid imide, nicotinanilide, nifenazone, nialamide, 1-(3-pyridylmethyl9 urea, nicornol and niaprazine or derivatives thereof is of interest for use as a pyridine carboxy derivative.

As stated above, these pyridine carboxy derivatives may optionally be further substituted or they may be provided as salts. In some embodiments, the pyridine ring may be substituted with an amino group or alkoxy group.

In the embodiment where the optionally substituted pyridine carboxy derivative is an amide, the amide may be its free primary amide (NH2), its secondary amide (NHR''') or its tertiary amide (NR'''R'''').

As stated, the pyridine carboxy derivative may be optionally substituted. In one suitable embodiment, the pyridine carboxy is further substituted with a carboxy group such as a carboxylic acid. Moreover, in interesting embodiments the pyridine carboxy is further substituted with alkoxyl, e.g. methoxy and ethoxy, amino, acyl, halide, carboxylic ester, or acetamide. The pyridine carboxy may be substituted 0 to 4 times, such as 0, 1, 2, 3, or 4 times, preferably 0 to 1 time, most preferably 0 times. In one embodiment thereof the pyridine carboxy derivative is 6-amino-nicotinamide or 6-methoxy-nicotinamide.

In a suitable embodiment of the invention, the chemical complex and the composition comprises more than one pyridine carboxy derivative.

As stated, the complex comprises, in part, the fatty acid ester of a polyhydroxyalkane. In a suitable embodiment of the invention, the chemical complex and the composition comprises more than one fatty acid ester of a polyhydroxyalkane.

As stated the combination of the two agents provides a surprisingly effective therapeutic agent for suppression of hypersensitivity and inflammatory reactions. The proper therapeutic efficacy may, in part, be adjusted by providing the two agents in suitable molar ratios or mass ratios.

Hence, the combination of a fatty acid ester of a polyhydroxyalkane and the pyridine carboxy derivative in a chemical complex or in a compositions according to the invention comprises adjustable molar ratio's between fatty acid ester of a polyhydroxyalkane and the pyridine carboxy derivative in the range of about 1:10000 to 10000:1. Preferably in the range of about 1:1000 to 1000:1, such as about 1:500 to 500:1, such as 1:100 to 100:1, about 1:50 to 50:1, or about 1:40 to 40:1, also about 1:30 to 30:1, such as about 1:25 to 25:1, about 1:20 to 20:1, about 1:18 to 18:1, about 1:16 to 16:1, about 1:14 to 14:1, or about 1:12 to 1:12, also about 1:10 to 10:1, such as about 1:9 to 9:1, about 1:8 to 8:1, about 1:7 to 7:1, about 1:6 to 6:1, also from 1:5 to 5:1, such as from 1:4 to 4:1, e.g. from 1:3 to 3:1, such as from 1:2 to 2:1.

Alternatively defined, the ratio between the fatty acid ester of a polyhydroxyalkane and the pyridine carboxy derivative may be expressed as a mass ratio. The mass ratio between the fatty acid ester of a polyhydroxyalkane and the pyridine carboxy derivative may be about 1:10000 to 10000:1, preferably about 1:1000 to 1000:1, such as about 1:500 to 500:1, such as 1:100 to 100:1, about 1:50 to 50:1, or about 1:40 to 40:1, also about 1:30 to 30:1, such as about 1:25 to 25:1, about 1:20 to 20:1, about 1:18 to 18:1, about 1:16 to 16:1, about 1:14 to 14:1, or about 1:12 to 1:12, also about 1:10 to 10:1, such as about 1:9 to 9:1, about 1:8 to 8:1, about 1:7 to 7:1, about 1:6 to 6:1, also from 1:5 to 5:1, such as from 1:4 to 4:1, e.g. from 1:3 to 3:1, such as from 1:2 to 2:1.

For the administration to a mammal, such as a human, the chemical complex may be administered directly, eventually provided in a capsule or the like. More convenient, the complex may be formulated into a composition comprising the chemical complex and optionally, one or more acceptable excipients. Alternatively, the combination of the two agents may also be formulated into a composition without being provided as a chemical complex. Thus, in some embodiments of the invention, the chemical complexes or compositions further comprise one of more excipient(s) or carrier(s), preferably pharmaceutically acceptable excipient(s) or carrier(s).

According to the invention, the above-mentioned chemical complexes or compositions may be combined with any other therapeutically active agents in order to strengthen, improve, potentiate, or prolong the therapeutic actions of said complexes and said compositions. Thus according to the invention, the composition may further comprise one or more therapeutically active agents. Therapeutically active agents of interest include those selected from the group consisting of antioxidants, steroids, antibiotics, anti-inflammatory agents and NSAID's.

The compositions according to the present invention may be further comprises one or more excipient(s) or carrier(s) for the formulation of the composition as a pharmaceutical, a dietary supplement or a cosmetic.

Thus, further aspects of the invention relates to the use of the combination of a fatty acid ester and a pyridine carboxy derivative as disclosed herein for use as a dietary supplement and/or a cosmetic. As is to be understood, the present combinations of components exhibit surprisingly activity in the alleviation of inflammation and infective conditions. Therefore, in further aspects, the invention relates to the cosmetic treatment of conditions that may be selected from the group consisting of acne, acne prone skin, irritated skin, dry skin, skin redness, scaly or flaking skin, and sunburned skin. Moreover, as may be understood, the present combination of components as disclosed herein may be used as an antiseptic agent, disinfectant, bacteriostatic agent, bactericidal agent, protective agent, and/or regenerating agent.

It is to be understood that the composition may be administered in several manners. Typically, a pharmaceutical may be formulated for oral, topical, transdermal, or parenteral administration, preferably oral or topical administration. The compositions according to the present invention may be formulated as a pharmaceutical composition for oral, topical, transdermal, or parenteral administration, preferably oral or topical administration.

In a suitable embodiment of the invention, the compositions are used for oral administration. In another suitable embodiment of the invention the compositions are used for topical administration.

Concerning compositions for cosmetic use, they may be formulated for application to skin or a mucous membrane such as to application to the mucous of the vagina, rectum, mouth or eyes. Moreover, the cosmetic use may imply peroral formulations of the compositions. Typically, the cosmetic formulations may be in the form of creams, lotions, gels, shampoo, conditioner, fluid soap, bar soap, cleansing products, shower and bath products.

In a preferred embodiment of the invention the compositions are formulated for topical administration (e.g. to the skin) in the form of emulsions (e.g. creams or lotions), gels, solutions, liniments, ointments, sprays, aerosols or powders.

The fatty acid ester of a polyhydroxyalkane and the pyridine carboxy derivative may together be comprised in a single formulation or may each individually be comprised in separate formulations. The separate formulations may be administered in a simultaneous or non-simultaneous manner. As stated, the fatty acid ester of a polyhydroxyalkane and the pyridine carboxy derivative are together comprised in a single formulation.

The active ingredients of the chemical complex or pharmaceutical composition of the present invention need not be administered as one pharmaceutical entity, but may of course be administered as individual compounds or pharmaceutical compositions.

In addition to the formulations described previously, the compositions of the invention may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions for oral, topical, transdermal, or parenteral administration may be in form of, e.g., solid, semi-solid or fluid compositions and formulated according to conventional pharmaceutical practice, see, e.g., "Remington: The science and practice of pharmacy" $20^{th}$ ed. Mack Publishing, Easton Pa., 2000 ISBN 0-912734-04-3 and "Encyclopedia of Pharmaceutical Technology", edited by Swarbrick, J. & J. C. Boylan, Marcel Dekker, Inc., New York, 1988 ISBN 0-8247-2800-9.

The choice of pharmaceutically acceptable excipients in a composition for use according to the invention and the optimum concentration thereof is determined on the basis of the selection of the Fatty acid ester of a polyhydroxyalkane, selection of the pyridine carboxy derivative, the kind of dosage form chosen and the mode of administration. However, a person skilled in the art of pharmaceutical formulation may find guidance in e.g., "Remington: The science and practice of pharmacy" $20^{th}$ ed. Mack Publishing, Easton Pa., 2000 ISBN 0-912734-04-3. A pharmaceutically acceptable excipient is a substance, which is substantially harmless to the individual to which the composition will be administered. Such an excipient suitably fulfils the requirements given by the national drug agencies. Official pharmacopeias such as the British Pharmacopeia, the United States of America Pharmacopeia and the European Pharmacopeia set standards for well-known pharmaceutically acceptable excipients.

For topical, trans-mucosal and trans-dermal compositions, such as administration to the mucosa or the skin, the compositions for use according to the invention may contain conventional non-toxic pharmaceutically acceptable carriers and excipients including microspheres and liposomes.

The topical, trans-mucosal and trans-dermal compositions for use according to the invention include an array of solid, semi-solid and fluid compositions. Compositions of particular relevance are e.g. pastes, ointments, hydrophilic ointments, creams, gels, hydrogels, solutions, emulsions, suspensions, lotions, liniments, resoriblets, suppositories, enema, pessaries, moulded pessaries, vaginal capsules, vaginal tablets, shampoos, jellies, soaps, sticks, sprays, powders, films, foams, pads, sponges (e.g. collagen sponges), pads, dressings (such as, e.g., absorbent wound dressings), drenches, bandages, plasters and transdermal delivery systems.

The pharmaceutically acceptable excipients for topical, trans-mucosal and trans-dermal compositions may include solvents, buffering agents, preservatives, humectants, chelating agents, antioxidants, stabilizers, emulsifying agents, suspending agents, gel-forming agents, ointment bases, suppository bases, penetration enhancers, perfumes, skin protective agents, diluents, disintegrating agents, binding agents, lubricants and wetting agents.

The oral compositions for use according to the invention include an array of solid, semi-solid and fluid compositions. Compositions of particular relevance are e.g. solutions, suspensions, emulsions, uncoated tablets, immediate-release tablets, modified-release tablets, gastro-resistant tablets, orodispersible tablets, effererscent tablets, chewable tablets, soft capsules, hard capsules, modified-release capsules, gastro-resistant capsules, uncoated granules, effervescent granules, granules for the preparation of liquids for oral use, coated granules, gastro-resistant granules, modified-release granules, powders for oral administration and powders for the preparation of liquids for oral use.

The pharmaceutically acceptable excipients may include solvents, vegetable or marine oils (e.g. edible oils like almond oil, castor oil, cacao butter, coconut oil, corn oil, cottonseed oil, linseed oil, olive oil, palm oil, peanut oil, poppyseed oil, rapeseed oil, sesame oil, soybean oil, sunflower oil, and teaseed oil), mineral oils, fatty oils, liquid paraffin, buffering agents, preservatives, humectants, chelating agents, antioxidants, stabilizers, emulsifying agents, suspending agents, gel-forming agents, diluents, disintegrating agents, binding agents, lubricants, coating agents and wetting agents.

Typical solvents may be selected from the group comprising water, alcohols, polyethylene glycols, propylene glycols, glycerol, liquid polyalkylsiloxanes, and mixtures thereof.

Typical buffering agents may be selected from the group comprising of citric acid, acetic acid, tartaric acid, lactic acid, hydrogenphosphoric acid, diethylamine etc.

Typical preservatives may be selected from the group comprising parabens, such as methyl, ethyl, propyl p-hydroxybenzoate, butylparaben, isobutylparaben, isopropylparaben, potassium sorbate, sorbic acid, benzoic acid, methyl benzoate, phenoxyethanol, bronopol, bronidox, MDM hydantoin, iodopropynyl butylcarbamate, EDTA, benzalconium chloride, and benzylalcohol, or mixtures of preservatives.

Typical humectants may be selected from the group comprising glycerin, propylene glycol, sorbitol, lactic acid, urea, and mixtures thereof. Typical chelating agents are but not limited to sodium EDTA and citric acid. Typical antioxidants may be selected from the group comprising butylated hydroxy anisole (BHA), ascorbic acid and derivatives thereof, tocopherol and derivatives thereof, cysteine, and mixtures thereof. Suitable emulsifying agents may be selected from the group comprising naturally occurring gums, e.g. gum acacia or gum tragacanth; naturally occurring phosphatides, e.g. soybean lecithin; sorbitan monooleate derivatives; wool fats; wool alcohols; sorbitan esters; monoglycerides; fatty alcohols, fatty acid esters (e.g. triglycerides of fatty acids); and mixtures thereof.

Suitable suspending agents may be selected from the group comprising celluloses and cellulose derivatives such as, e.g., carboxymethyl cellulose, hydroxyethylcellulose, hydroxypropylcellulose, hydroxypropylmethylcellulose, carrageenan, acacia gum, arabic gum, tragacanth, and mixtures thereof.

Suitable gel bases and viscosity-increasing components may be selected from the group comprising liquid paraffin, polyethylene, fatty oils, colloidal silica or aluminium, zinc soaps, glycerol, propylene glycol, tragacanth, carboxyvinyl polymers, magnesium-aluminium silicates, Carbopol®, hydrophilic polymers such as, e.g. starch or cellulose derivatives such as, e.g., carboxymethylcellulose, hydroxyethylcellulose and other cellulose derivatives, water-swellable hydrocolloids, carragenans, hyaluronates (e.g. hyaluronate gel optionally containing sodium chloride), and alginates including propylene glycol alginate.

Typical ointment bases may be selected from the group comprising beeswax, paraffin, cetanol, cetyl palmitate, vegetable oils, sorbitan esters of fatty acids (Span), polyethylene glycols, and condensation products between sorbitan esters of fatty acids and ethylene oxide, e.g. polyoxyethylene sorbitan monooleate (Tween).

Typical hydrophobic ointment bases may be selected from the group comprising paraffins, vegetable oils, animal fats, synthetic glycerides, waxes, lanolin, and liquid polyalkylsiloxanes. Typical hydrophilic ointment bases are but not limited to solid macrogols (polyethylene glycols).

Suitable powder components may be selected from the group comprising alginate, collagen, lactose, powder, which is able to form a gel when applied to a wound (absorbs liquid/wound exudate).

Suitable diluents and disintegrating agents may be selected from the group comprising lactose, saccharose, emdex, calcium phosphates, calcium carbonate, calcium sulphate, mannitol, starches and microcrystaline cellulose.

Suitable binding agents may be selected from the group comprising saccharose, sorbitol, gum acacia, sodium alginate, gelatine, starches, cellulose, sodium carboxymethylcellulose, methylcellulose, hydroxypropylcellulose, polyvinylpyrrolidone and polyethyleneglycol.

Typical wetting agents may be selected from the group comprising sodium laurylsulphate and polysorbate 80.

Suitable lubricants may be selected from the group comprising talcum, magnesium stearate, calcium stearate, silicium oxide, precirol and polyethylenglycol.

Suitable coating agents may be selected from the group comprising hydroxypropylcellulose, hydroxypropylmethylcellulose, polyvinylpropylidone, ethylcellulose and polymethylacrylates.

Typical suppository bases may be selected from the group comprising oleum cacao, adeps solidus and polyethylenglycols.

The present inventor has recognised the therapeutic effect of the complexes and compositions of this invention, partly by observing the reduced inflammation of sub-chronic phorbol ester induced inflamed mouse ear upon administering the complexes and compositions. This test model is a commonly employed method for evaluation of anti-inflammatory drugs for chronic inflammatory conditions.

The acute anti-inflammatory activity was demonstrated in the TPA induced ear inflammation test in mice, which is a commonly employed method for screening and evaluation of antiinflammatory drugs. This model has broad relevance to inflammatory reactions that occur in various hypersensitivity, allergic and autoimmune diseases. Furthermore TPA is known to induce cancer in mice and substances that inhibit TPA induced inflammation thus also inhibit the formation of cancer.

Thus, in a broad sense the chemical complexes or compositions provides an immunomodulating effect. Moreover, the inventor has recognised that a number of diseases or conditions with similarities in the etiology of the inflammatory reactions that are provoked in the sub-chronic phorbolester induced inflamed mouse ear may be effectively treated by the present complexes and compositions of the invention. Such diseases and conditions relate in general to those associated with hypersensitivity reactions and inflammatory reactions. In a more specific sense, the chemical complexes or compositions of the invention provides suppression of hypersensitivity reactions, suppression of inflammatory reactions, suppression of IgE mediated allergic reactions, suppression of autoimmune reactions, reduction of pain, and suppression of cancer.

Hence, a further aspect of the invention relates to a method for immunomodulation in a mammal, such as a human, comprising the administration to said mammal of an effective amount of a combination of a fatty acid ester of a polyhydroxyalkane and a pyridine carboxy derivative, or a chemical complex comprising a fatty acid ester of a polyhydroxyalkane and a pyridine carboxy derivative.

As used herein, the term "effective amount" relates to the effective dose to be determined by a qualified practitioner, who may titrate dosages to achieve the desired response. Factors for consideration of dose will include potency, bioavailability, desired pharmacokinetic/pharmacodynamic profiles, condition of treatment, patient-related factors (e.g. weight, health, age, etc.), presence of co-administered medications (e.g., anticoagulants), time of administration, or other factors known to a medical practitioner.

As used herein, the term "treatment" relates to treatment of symptoms or prevention the relapse of symptoms in a person diagnosed with a disease related to inflammation, hypersensitivity, infection, cancer and/or pain.

A still further aspect relates to a method for the treatment of infections or diseases associated with infections selected from the group consisting of microbial infections, viral infections, infections caused by parasites, infections caused by fungi in a mammal, such as a human, comprising the administration to said mammal an effective amount of a combination of a fatty acid ester and a pyridine carboxy derivative as disclosed herein.

As stated the complexes and compositions according to the invention may be applicable for the preparation of a medicament. Thus, other aspects of the invention relates to the use of a combination of a fatty acid ester and a pyridine carboxy derivative for the preparation of a medicament for the treatment of infections or diseases associated with infections selected from the group consisting of microbial infections, viral infections, infections caused by parasites, infections caused by fungi in a mammal, such as a human.

As recognised by the present inventor, the combination of components as disclosed herein may be used for the treatment of a disease and disorder associated with hypersensitivity and/or inflammatory reactions or conditions, such as a disease and a disorder that may be selected from the group consisting of hypersensitivity skin disease, pruritus, urticaria, atopic eczema, contact dermatitis, seborrhoeic dermatitis, acne, rosacea, alopecia, vitiligo, psoriasis IgE mediated allergic reactions, asthma, allergic rhinitis, anaphylaxis, autoimmune disease, chronic inflammatory disease, Crohn's disease, ulcerative colitis, rheumatoid arthritis, gout, osteoarthritis, inflammation associated with pain and inflammation associated with cancer.

For illustrative purposes, the treatment of inflammatory conditions relates to the treatment of Autoimmune hepatitis, Primary biliary cirrhosis, Primary sclerosing cholangitis, Autoimmune hemolytic anemias, Grave's disease, Myasthenia gravis, Type 1 Diabetes Mellitus, Inflammatory myopathies, Multiple sclerosis, Hashimoto's thyreoiditis, Autoimmune adrenalitis, Crohn's Disease, Ulcerative Colitis, Glomerulonephritis, Progressive Systemic Sclerosis (Scleroderma), Sjögren's Disease, Lupus Erythematosus, Primary vasculitis, Rheumatoid Arthritis, Juvenile Arthritis, Mixed Connective Tissue Disease, Psoriasis, Pemfigus, Pemfigoid, and Dermatitis Herpetiformis.

The therapeutic action of the complexes and compositions of the invention may be relevant to diseases associated with hypersensitivity reactions or inflammation in general.

Particularly, the treatment of hypersensitivity relates to the treatment of infections (viral, bacterial, fungal, parasitic), cold and flu, contact dermatitis, insect bites, allergic vasculitis, post-operative reactions, transplantation rejection (graft-versus-host disease), and so forth.

Treatment of IgE mediated allergic reaction or condition relates to the treatment of asthma, eczema (e.g. atopic dermatitis), urticaria, allergic rhinitis and anaphylaxis.

Accordingly, the complexes or compositions of the invention are particularly suitable for the treatment of inflammatory skin diseases associated with secondary infections, e.g. seborrhoeic dermatitis, atopic dermatitis, acne, rosacea, psoriasis, etc. Such secondary infections may often occur in association with any inflammatory condition of the skin or mucous membranes.

Moreover, the chemical complex or composition of the present invention may be used in a method for the treatment or prevention of pain associated with inflammation. The applicant proposes the hypothesis that the therapeutic action is related to immunomodulation, possibly to a suppressing effect on hypersensitivity reactions.

As mentioned, a still further aspect of the invention relates to the treatment of the treatment of infections or diseases associated with infections selected from the group consisting of microbial infections, viral infections, infections caused by parasites, infections caused by fungi in a mammal, comprising administration of the combination of components as disclosed herein. A broad spectrum of antibacterial, antifungal, antiviral and antiparasital effects can be anticipated.

In one aspect the invention relates to the treatment of bacterial infections or diseases associated with bacterial infections in a mammal. Relevant but non-limiting examples of target organisms include: gram positive bacteria e.g. *Baccillus subtilis, Brevibacterium ammoniagenes, Corynebacterium minutissimum, Enterococcus faecalis, Enterococcus faecalis, Micrococcus luteus, Mycobacterium phlei, Mycobacterium ranae, Staphylococcus aureus, Staphylococcus aureus* (Methicillin Resistant), *Staphylococcus aureus, Staphylococcus epidermidis, Streptococcus faecalis, Streptococcus mutans, Streptococcus pneumoniae, Streptococcus pneumoniae;* gram negative bacteria e.g. *Enterobacter cloacae, Escherichia coli, Escherichia coli, Klebsiella pneumoniae, Proteus vulgaris, Pseudomonas aeruginosa, Salmonella typhimurium, Serratia marcescens;* anaerobes e.g. *Actinomyces viscosus, Bacteroides fragilis, Clostridium sporogenes, Corynebacterium acnes, Helicobacter pylori;* fungi e.g. *Aspergillus fumigatus, Candida albicans, Candida glabrata, Crytococcus neoformans, Epidermophyton floccosum, Exophiala jeanselmei, Microsporum canis, Microsporum gypseum, Trichophyton mentagrophytes, Trichophyton rubrum, Aspergillus niger, Cladosporium argillaceum, Mucor hiemalis, Mucor pusillus, Paecilomyces varioti, Penicillum chrysogenum, Penicillum citrinum, Pityrosporum ovale, Rhizopus nigricans* and *Saccharomyces cerevisiae.*

Thus, in some embodiments, the treatment, alleviation or prevention of infection with gram positive bacteria or a disease associated with infection with gram positive bacteria may be selected from the group consisting of *Baccillus subtilis, Brevibacterium ammoniagenes, Corynebacterium minutissimum, Enterococcus faecalis, Enterococcus faecalis, Micrococcus luteus, Mycobacterium phlei, Mycobacterium ranae, Staphylococcus aureus, Staphylococcus epidermidis, Streptococcus faecalis, Streptococcus mutans* and *Streptococcus pneumoniae* and the treatment, alleviation or prevention of infection with gram positive bacteria or a disease associated with infection with gram negative or anaerobe bacteria may be selected from the group consisting of *Enterobacter cloacae, Escherichia coli, Escherichia coli, Klebsiella pneumoniae, Proteus vulgaris, Pseudomonas aeruginosa, Salmonella typhimurium, Serratia marcescens, Actinomyces viscosus, Bacteroides fragilis, Clostridium sporogenes, Corynebacterium acnes* and *Helicobacter pylori*.

The combination of a fatty acid ester of formula I and a pyridine carboxy derivative of formula II may be useful in the treatment of fungal infections or diseases associated with fungal infections in a mammal such as for the treatment, alleviation or prevention of infection with fungi or a disease associated with infection with fungi that may be selected from the group consisting of *Aspergillus fumigatus, Candida albicans, Candida glabrata, Crytococcus neoformans, Epidermophyton floccosum, Exophiala jeanselmei, Microsporum canis, Microsporum gypseum, Trichophyton mentagrophytes, Trichophyton rubrum, Aspergillus niger, Cladosporium argillaceum, Mucor hiemalis, Mucor pusillus, Paecilomyces varioti, Penicillium chrysogenum, Penicillium citrinum, Pityrosporum ovale, Rhizopus nigricans* and *Saccharomyces cerevisiae*.

The therapeutic action of the complexes of the invention may also be relevant to all known or unknown viral infections or diseases caused by viruses, including both RNA and DNA viruses. Viruses of particular relevance to the present invention include herpesviruses, adenoviruses, papovaviruses, parvoviruses, picornaviruses, reoviruses, togaviruses, bunyaviruses, orthomyxoviruses, paramyxoviruses, rhabdoviruses, retroviruses, arenaviruses, poxviruses, hepadnaviruses, caliciviruses, flaviviruses, coronaviruses, filoviruses or orthomyxoviruses. Thus, the invention preferably provides a method as described above for the treatment or prevention of infection with herpesviruses, adenoviruses, papovaviruses, parvoviruses, picornaviruses, reoviruses, togaviruses, bunyaviruses, orthomyxoviruses, paramyxoviruses, rhabdoviruses, retroviruses, arenaviruses, poxviruses, hepadnaviruses, caliciviruses, flaviviruses, coronaviruses, filoviruses or orthomyxoviruses in an individual.

Even more preferred, the invention provides a method as described above for the treatment or prevention of infection with rhinovirus, influenzavirus, hepatitisvirus, herpesvirus or cytomegalovirus in an individual.

In another preferred embodiment, the present invention also provides a method as described above for the treatment or prevention of common cold, influenza, viral pharyngitis, viral pneumonia, or viral hepatitis in an individual.

Moreover, the chemical complexes or compositions of the invention are suitable for the treatment or prevention of diseases caused by inflammation of various tissues, such as the inflammation of the prostate, in particular prostatitis. The complexes and compositions of the invention are also suitable for the treatment or prevention of diseases associated with inflammation, pruritus (itch), erythema or hyperproliferation of the skin especially when topical administration is employed.

Furthermore, immunomodulation relates to the treatment of autoimmune disease and/or chronic inflammatory disease, at least in part, for the treatment or prevention of diabetes, Crohn's disease, ulcerative colitis, rheumatoid arthritis, gout or osteoarthritis.

Still further, the chemical complexes or compositions of the invention may be employed for the treatment or prevention of cancer associated with inflammation of any type and at any stage. The present inventor puts forward the hypothesis that the anticancer effect is due to a combination of immunomodulating and tumour-suppressing effects of the complexes and compositions of the invention.

EXAMPLES

The following examples describe the preparation of chemical complexes of the present invention.

General Method Examples 1-100

The fatty acid mono- or di-esters of a polyhydroxyalkane and the pyridine carboxy derivative are dissolved in as little solvent as possible. The solvent is removed by spray drying or freeze-drying. After the solvent is removed the product is a white to yellowish paste or powder.

The solvent is water:acetone in any v/v % combination.

The paste or powder is suitable for any type of product e.g. pharmaceutical products, dietary supplements and cosmetic formulations. Non-limiting examples of such products are tablets, capsules, ointments and lotions as described above.

Examples 1 to 10

Molar Ratio Fatty Acid Mono- or Di-Esters of a Polyhydroxyalkane/Pyridine Carboxy Derivative 1:10000 (Mol/Mol)

|  | Fatty acid mono- or di-esters of a polyhydroxyalkane 1 mol. | Pyridine carboxy derivative 10000 mol. |
|---|---|---|
| Example 1. | Ethyleneglycyl-1-hexanoate | Niacinamide |
| Example 2. | Ethylenglycyl-1-(4-noneoate) | Niacinamide |
| Example 3. | Glyceryl-1-heptanoate | N2-methyl-niacinamide |
| Example 4. | Glyceryl-2-(5-ethyl-octanoate) | N2-ethyl-niacinamide |
| Example 5. | Trimethylenglycyl-1-dodecanoate-2-dodecanoate | Aminoniacinamide |
| Example 6. | Trimethylenglycyl-1-octadecanoate-2-(5,7,9-heptadecatrienoate) | Thioniacinamide |
| Example 7. | 1,2,3,4-butantetraol-1-undecanoate-3-nonanoate | Aminoniacinamide |
| Example 8. | 1-ol-2,3-butylenglycyl-1-heptandecanoate-2-heptandecanoate | Niacinamide |
| Example 9. | Propylenglycyl-2-(3-methyl-decanoate) | N2-methyl-niacinamide |
| Example 10. | 1,2-butylenglycyl-1-hexanoate-2-hexanoate | Niacinamide |

Examples 11 to 20

Molar Ratio Fatty Acid Mono- or Di-Esters of a Polyhydroxyalkane/Pyridine Carboxy Derivative 1:5000 (Mol/Mol)

|  | Fatty acid mono- or di-esters of a polyhydroxyalkane 1 mol. | Pyridine carboxy derivative 5000 mol. |
|---|---|---|
| Example 11. | Ethyleneglycyl-1-octanoate | Niacinamide |
| Example 12. | Ethylenglycyl-1-octanoate-4-(3-ethyl-hexanoate) | Thioniacinamide |

Examples 13–20 (continued)

| | Fatty acid mono- or di-esters of a polyhydroxyalkane 1 mol. | Pyridine carboxy derivative 5000 mol. |
|---|---|---|
| Example 13. | 1,2,3,4-butantetraol-1-hexadecanoate-(4-(2,4-diethyl-8-hexadecenoate) | Thioniacinamide |
| Example 14. | 1,2,3,4-butanetetraol-2-eicosatrienoate | Aminoniacinamide |
| Example 15. | Glyceryl-1-decanoate-2-decanoate | Niacinamide |
| Example 16. | 1,4-butylenglycyl-1-octanoate | N2-methyl-niacinamide |
| Example 17. | 1-ol-2,3-butylenglycyl-1-heptandecanoate-2-heptandecanoate | N2-methyl-niacinamide |
| Example 18. | Propylenglycyl-1-undecanoate-2-undecanoate | Aminoniacinamide |
| Example 19. | Propylenglycyl-1-(7,10-octadecadienoate)-2-octanoate | Niacinamide |
| Example 20. | Glyceryl-2-(8,11,14-eicosatrienoate) | N2-methyl-niacinamide |

Examples 21 to 30

Molar Ratio Fatty Acid Mono- or Di-Esters of a Polyhydroxyalkane/Pyridine Carboxy Derivative 1:1000 (Mol/Mol)

| | Fatty acid mono- or di-esters of a polyhydroxyalkane 1 mol. | Pyridine carboxy derivative 1000 mol. |
|---|---|---|
| Example 21. | Ethylenglycyl-1-decanoate-2-hexanoate | Niacinamide |
| Example 22. | Ethylenglycyl-1-(4-tetradecenoate) | Niacinamide |
| Example 23. | Glyceryl-1-octanoate-3-undecanoate | N2-methyl-niacinamide |
| Example 24. | Glyceryl-1-(4-nonenoate)-3-hexanoate | N2-ethyl-niacinamide |
| Example 25. | Trimethylglycyl-1-octanoate | Aminoniacinamide |
| Example 26. | Trimethylenglycyl-1-undecanoate | Thioniacinamide |
| Example 27. | Propylenglycyl-1-hexanoate | Aminoniacinamide |
| Example 28. | Propylenglycyl-2-(3-methyl-decanoate) | Niacinamide |
| Example 29. | 1,2-butylenglycyl-2-octanoate | N2-methyl-niacinamide |
| Example 30. | 1,2-butylenglycyl-1-nonaoate-2-octanoate | Niacinamide |

Examples 31 to 40

Molar Ratio Fatty Acid Mono- or Di-Esters of a Polyhydroxyalkane/Pyridine Carboxy Derivative 1:500 (Mol/Mol)

| | Fatty acid mono- or di-esters of a polyhydroxyalkane 1 mol. | Pyridine carboxy derivative 216 mol. |
|---|---|---|
| Example 31. | 1,3-butylenglycyl-1-decanoate-3-octanoate | Aminoniacinamide |
| Example 32. | 2,3-butylenglycyl-2-dodecanoate | Niacinamide |
| Example 33. | 2,3-butylenglycyl-2-octanoate-3-octanoate | Thioniacinamide |
| Example 34. | Ethylenglycyl-1-(3,6-octadecadienoate)-2-octanoate | Niacinamide |
| Example 35. | Ethylenglycyl-1-(8-methyl-3,6-octadecadienoate) | N2-ethyl-niacinamide |
| Example 36. | Glyceryl-1-(4,6,10-eicosatrienoate)-2-(4,6,10-eicosatrienoate) | Thioniacinamide |
| Example 37. | Glyceryl-1-(8-octadecenoate)-3-heptanoate | Niacinamide |
| Example 38. | Trimethylenglycyl-2-(4-methyl-2,8-eicosadienoate) | Niacinamide |
| Example 39. | Propylenglycyl-1-nonanoate | N2-ethyl-niacinamide |
| Example 40. | 1,2,3,4-butantetraol-1-decanoate | Thioniacinamide |

Examples 41 to 50

Molar Ratio Fatty Acid Mono- or Di-Esters of a Polyhydroxyalkane/Pyridine Carboxy Derivative 1:100 (Mol/Mol)

| | Fatty acid mono- or di-esters of a polyhydroxyalkane 1 mol. | Pyridine carboxy derivative 100 mol, |
|---|---|---|
| Example 41. | 1,2,3,4-butantetraol-1-hexadecanoate-(4-(2,4-diethyl-8-hexadecenoate) | Niacinamide |
| Example 42. | 1,2,3,4-butanetetraol-2-eicosatrienoate | Thioniacinamide |
| Example 43. | 2,3-butylenglycyl-2-hexanoate | N2-methyl-niacinamide |
| Example 44. | 1-ol-2,3-butylenglycyl-1-(4-methyl-hexanoate) | N2-ethyl-niacinamide |
| Example 45. | 1-ol-2,3-butylenglycyl-1-(3-octenoate) | Thioniacinamide |
| Example 46. | 1,4-butylenglycyl-1-dodecanoate | Aminoniacinamide |
| Example 47. | 1,4-butylenglycyl-1-decanoate-4-decanoate | Niacinamide |
| Example 48. | 1,2,3,4-butantetraol-2-(2-methyl-octanoate) | Niacinamide |
| Example 49. | 1,2,3,4-butantetraol-1-hexanoate-2-hexanoate | Aminoniacinamide |
| Example 50. | Glyceryl-2-(3,5,7-hexadecatrienoate) | Thioniacinamide |

Examples 51 to 60

Molar Ratio Fatty Acid Mono- or Di-Esters of a Polyhydroxyalkane/Pyridine Carboxy Derivative 1:14 (Mol/Mol)

| | Fatty acid mono- or di-esters of a polyhydroxyalkane 2 mol. | Pyridine carboxy derivative 7 mol. |
|---|---|---|
| Example 51. | Glyceryl-1-octanoate | Niacinamide |
| Example 52. | Glyceryl-2-octanoate | Niacinamide |
| Example 53. | Glyceryl-1-heptanoate | Aminoniacinamide |
| Example 54. | Glyceryl-1-octanoate-2-octanoate | Thioniacinamide |
| Example 55. | Glyceryl-2-(3,5,7-hexadecatrienoate) | N2-methyl-niacinamide |

-continued

|  | Fatty acid mono- or di-esters of a polyhydroxyalkane 2 mol. | Pyridine carboxy derivative 7 mol. |
|---|---|---|
| Example 56. | Glyceryl-1-(3-ethyl-2-methyl-8,10-eicosadienoate)-2-octanoate | Aminoniacinamide |
| Example 57. | Propylenglycyl-1-(2,4-ethyl-6-tetradecaenoate)-2-(8,12-hexadecaenoate) | Thioniacinamide |
| Example 58. | 1,2-butylenglycyl-1-decanoate | N2-methyl-niacinamide |
| Example 59. | 1,2-butylenglycyl-1-heptadecanoate-2-(4,8-heptadecadienoate) | Niacinamide |
| Example 60. | 1,2-butylenglycyl-1-(8-ethyl-4-methyl-6,16-octadecadienoate) | Thioniacinamide |

Examples 61 to 70

Molar Ratio Fatty Acid Mono- or Di-Esters of a Polyhydroxyalkane/Pyridine Carboxy Derivative 1:1 (Mol/Mol)

|  | Fatty acid mono- or di-esters of a polyhydroxyalkane 1 mol, | Pyridine carboxy derivative 1 mol. |
|---|---|---|
| Example 61. | Glyceryl-1-(5,8,11,14,17-eicosapentaenoate) | Niacinamide |
| Example 62. | Propylenglycyl-1-nonanoate-2-decanoate | Thioniacinamide |
| Example 63. | Trimethylenglycyl-1-octanoate-2-(4-ethyl-decanoate) | N2-methyl-niacinamide |
| Example 64. | 1,3-butylenglycyl-1-undecanoate | N2-ethyl-niacinamide |
| Example 65. | 1,3-butylenglycyl-3-hexanoate | Thioniacinamide |
| Example 66. | 1,3-butylenglycyl-1-octanoate-3-octanoate | Aminoniacinamide |
| Example 67. | 1-ol-2,3-butylenglycyl-1-undecanoate-2-undecanoate | Niacinamide |
| Example 68. | 1-ol-2,3-butylenglycyl-1-(2-ethyl-nonanoate)-2-hexanoate | Thioniacinamide |
| Example 69. | Glyceryl-2-octanoate | N2-methyl-niacinamide |
| Example 70. | Glyceryl-1-octanoate-2-octanoate | N2-ethyl-niacinamide |

Examples 71 to 80

Molar Ratio Fatty Acid Mono- or Di-Esters of a Polyhydroxyalkane/Pyridine Carboxy Derivative 5:1 (Mol/Mol)

|  | Fatty acid mono- or di-esters of a polyhydroxyalkane 5 mol. | Pyridine carboxy derivative 1 mol. |
|---|---|---|
| Example 71. | 1,4-butylenglycyl-1-octanoate-4-heptanoate | Thioniacinamide |
| Example 72. | 2,3-butylenglycyl-2-dodecanoate-3-heptanoate | Aminoniacinamide |
| Example 73. | 1,2,3,4-butantetraol-2-(2-methyl-octanoate) | Niacinamide |
| Example 74. | 1,2,3,4-butantetraol-1-hexanoate-2-hexanoate | Thioniacinamide |
| Example 75. | 1,4-butylenglycyl-1-(6,10,12,18-tetradecantetraenoate)-4-(4,8-dimethyl-6,13-eicosadienoate) | N2-methyl-niacinamide |

-continued

|  | Fatty acid mono- or di-esters of a polyhydroxyalkane 5 mol. | Pyridine carboxy derivative 1 mol. |
|---|---|---|
| Example 76. | 1,4-butylenglycyl-1-(2-ethyl-octanoate)-4-(4-nonenoate) | N2-ethyl-niacinamide |
| Example 77. | Glyceryl-1-octanoate | Thioniacinamide |
| Example 78. | Glyceryl-1-(5,8,11,14,17-eicosapentaenoate) | Aminoniacinamide |
| Example 79. | Glyceryl-2-(8,11,14-eicosatrienoate) | Niacinamide |
| Example 80. | 1,2,3,4-butantetraol-2-(2-methyl-octanoate) | Niacinamide |

Examples 81 to 85

Molar Ratio Fatty Acid Mono- or Di-Esters of a Polyhydroxyalkane/Pyridine Carboxy Derivative 50:1 (Mol/Mol)

|  | Fatty acid mono- or di-esters of a polyhydroxyalkane 50 mol. | Pyridine carboxy derivative 1 mol. |
|---|---|---|
| Example 81. | Ethyleneglycyl-1-octanoate | Thioniacinamide |
| Example 82. | Ethylenglycyl-1-octanoate-4-(3-ethyl-hexanoate) | Aminoniacinamide |
| Example 83. | Glyceryl-1-octanoate | Niacinamide |
| Example 84. | Glyceryl-1-(5,8,11,14,17-eicosapentaenoate) | Thioniacinamide |
| Example 85. | Glyceryl-2-(8,11,14-eicosatrienoate) | N2-methyl-niacinamide |

Examples 86 to 90

Molar Ratio Fatty Acid Mono- or Di-Esters of a Polyhydroxyalkane/Pyridine Carboxy Derivative 500:1 (Mol/Mol)

|  | Fatty acid mono- or di-esters of a polyhydroxyalkane 500 mol. | Pyridine carboxy derivative 1 mol. |
|---|---|---|
| Example 86. | Glyceryl-2-(8,11,14-eicosatrienoate) | Thioniacinamide |
| Example 87. | 1,2,3,4-butantetraol-2-(2-methyl-octanoate) | Aminoniacinamide |
| Example 88. | Glyceryl-1-octanoate | Niacinamide |
| Example 89. | Trimethylenglycyl-2-(4-methyl-2,8-eicosadienoate) | Thioniacinamide |
| Example 90. | Propylenglycyl-1-nonanoate | N2-methyl-niacinamide |

Examples 91 to 96

Molar Ratio Fatty Acid Mono- or Di-Esters of a Polyhydroxyalkane/Pyridine Carboxy Derivative 1000:1 (Mol/Mol)

|  | Fatty acid mono- or di-esters of a polyhydroxyalkane 1000 mol. | Pyridine carboxy derivative 1 mol. |
| --- | --- | --- |
| Example 91. | Glyceryl-1-(5,8,11,14,17-eicosapentaenoate) | Thioniacinamide |
| Example 92. | Propylenglycyl-1-(2,4-ethyl-6-tetradecaenoate)-2-(8,12-hexadecanoate) | Aminoniacinamide |
| Example 93. | 1,2-butylenglycyl-1-decanoate | Niacinamide |
| Example 94. | 1,2-butylenglycyl-2-octanoate | Thioniacinamide |
| Example 95. | Glyceryl-2-octanoate | N2-methyl-niacinamide |
| Example 96. | 1,4-butylenglycyl-1-decanoate-4-decanoate | N2-ethyl-niacinamide |

Examples 97 to 100

Molar Ratio Fatty Acid Mono- or Di-Esters of a Polyhydroxyalkane/Pyridine Carboxy Derivative 10000:1 (Mol/Mol)

|  | Fatty acid mono- or di-esters of a polyhydroxyalkane 10000 mol. | Pyridine carboxy derivative 1 mol. |
| --- | --- | --- |
| Example 97. | Glyceryl-2-octanoate | Thioniacinamide |
| Example 98. | Ethylenglycyl-1-decanoate-2-hexanoate | Aminoniacinamide |
| Example 99. | 1-ol-2,3-butylenglycyl-1-(2-ethyl-nonanoate)-2-hexanoate | Niacinamide |
| Example 100. | Glyceryl-2-(8,11,14-eicosatrienoate) | Thioniacinamide |

General Method Examples 101-110

A lotion with a quantity of the Fatty acid mono- or di-esters of a polyhydroxyalkane and the pyridine carboxy derivative are made.

A lotion of the following composition (w/w) % is made

| Water: | 60.9% |
| --- | --- |
| Complex: | 5.0% |
| Methylparabene: | 0.1% |
| Tefose 63 (Gattefossé): | 12.0% |
| Arachis oil: | 10.0% |
| Isopropylmyristat (16): | 10.0% |
| Sodium stearoyl lactylate: | 2.0% |

Examples 101 to 103

100 g lotion containing 5% (w/w) of a complex comprising a fatty acid mono- or di-ester of a polyhydroxyalkane and pyridine carboxy derivative in a weight ratio of 1:2 (w/w).

|  | Fatty acid mono- or di-esters of a polyhydroxyalkane 1.665 g | Pyridine carboxy derivative 3.335 g |
| --- | --- | --- |
| Example 101. | Glyceryl-2-octanoate 1.665 g | Thioniacinamide 3.335 g |
| Example 102. | Glyceryl-2-(8,11,14-eicosatrienoate) 1.665 g | Aminoniacinamide 3.335 g |
| Example 103. | Ethylenglycyl-1-decanoate-2-hexanoate 1.665 g | N2-ethyl-niacinamide 3.335 g |

Examples 104 to 106

100 g lotion containing 10% (w/w) of a complex comprising a fatty acid mono- or di-ester of a polyhydroxyalkane and a pyridine carboxy derivative in a weight ratio of 1:2 (w/w).

|  | Fatty acid mono- or di-esters of a polyhydroxyalkane 3.333 g | Pyridine carboxy derivative 6.667 g |
| --- | --- | --- |
| Example 104. | Glyceryl-1-octanoate-2-octanoate 3.333 g | Thioniacinamide 6.667 g |
| Example 105. | Glyceryl-1-(5,8,11,14,17-eicosapentaenoate) 3.333 g | Aminoniacinamide 6.667 g |
| Example 106. | Glyceryl-2-(8,11,14-eicosatrienoate) 3.333 g | N2-ethyl-niacinamide 6.667 g |

Examples 107 to 110

500 g lotion containing 5% (w/w) of a complex comprising a fatty acid mono- or di-ester of a polyhydroxyalkane and a pyridine carboxy derivative in a molar ratio of 2:7 (mol/mol).

|  | Fatty acid mono- or di-esters of a polyhydroxyalkane | Pyridine carboxy derivative |
| --- | --- | --- |
| Example 107. | Glyceryl-1-octanoate 218.3 g/mol 8.451 g | Niacinamide 122.13 g/mol 16.549 g |
| Example 108. | Glyceryl-2-octanoate 218.3 g/mol 8.451 g | Niacinamide 122.13 g/mol 14.136 g |
| Example 109. | 1,3-butylenglycyl-3-hexanoate 188.27 g/mol 7.043 g | Aminoniacinamide 137.14 g/mol 17.957 g |
| Example 110. | Glyceryl-1-octanoate-2-octanoate 328.5 g/mol 10.864 g | Thioniacinamide 138.19 g/mol 18.779 g |

Example 111

Investigation of a complex according to the invention in a recognized pharmacodynamic model of acute dermal inflammation.

Objective

The objective of this study was to assess the therapeutic value of combining the two types of active entities in the complexes of the invention. This was done by comparing a high dose, corresponding to $E_{max}$ (the maximal obtainable effect representing the plateau of the dose-response curve) with the individual effects of the molar amount present of each component of the complex. If the effect of the complex is higher than the sum of the components the effect is synergistic. The animal model chosen was the acute 12-O-tetradecanoylphorbol-13-acetate (TPA) induced mouse ear inflammation model (Rao T S et al. *Inflammation* 1993, 17(6): 723-41). Ear swelling in this model is strongly correlated with mediators that play a crucial role in the pathogenesis if human skin diseases and the relative potency of topical steroids is well correlated with their relative potency in humans. The positive control used in this study was betamethasone 17-valerate applied as a commercial preparation with maximum human dose (Celeston® Cutaneous Solution 0.1%, Shering-Plough). Betamethasone 17-valerate is one of the strongest topical steroids on the market and can only be used for a few weeks at a time due to serious adverse effects.

Test Articles and Vehicle

The test article is the complex prepared according to example 51 (Compound 51 in the following). All substances were obtained from Astion A/S, Denmark.

Animals

The study was performed in 40 female BALB/ca mice from M & B A/S, DK-8680 Ry. At start of the acclimatisation period the mice were in the weight range of 20 g (+/−5 g).

Housing

The study took place in an animal room provided with filtered air. The temperature in the room was set at 21-23° C. and the relative humidity to ≧30%. The room was illuminated to give a cycle of 12 hours light and 12 hours darkness. Light was on from 06.00 till 18.00 h.

The animals were housed in Macrolon type III cages (40× 25×14 cm), 10 in each cage. The cages were cleaned and the bedding changed at least once a week.

Bedding

The bedding was sawdust (Tapvei 4HV) from Tapvei Oy, 73620 Kortteinen, Finland.

Diet

A complete pelleted rodent diet "Altromin 1324" from Chr. Petersen, DK-4100 Ringsted, was available ad libitum.

Drinking Water

The animals had free access to bottles with domestic quality drinking water. The drinking water was changed daily.

Animal Randomisation and Allocation

On the day of arrival the animals were randomly allocated to groups of 10 mice.

Body Weight

The animals were weighed on the day of dosing and termination of the study.

Procedure

The test substances were administered 20 minutes before and 20 minutes after application of TPA to the ear.

All groups were treated with 20 µl TPA solution 400 µg/ml in acetone, on the right ear.

The groups (n=10) and doses were as follows:

| Group | Drug | Dose |
|---|---|---|
| 1 | Vehicle | — |
| 2 | Niacinamide | 64.1 µmol/ear |
| 3 | Rac-1-glyceryl-monocaprylate | 4.58 µmol/ear |
| 4 | Compound 51 | 4.58 µmol/ear |
| 5 | Betamethasone 17-valerate | 0.02 mg/ear |

Three hours after the TPA application the mice were sacrificed, the ears cut from the tip with a punch biopsy knife (8 mm diameter) and weighed.

Mean weights and standard deviations were calculated. Relative ear oedema was assessed as the weight difference between right and left ear of each mouse expressed as percent of the left ear. Percent inhibition of the relative ear oedema compared with the vehicle treated groups was calculated for the test substance and positive control treated group.

Clinical Signs

All visible signs of ill health and any behavioural changes were recorded daily during the study. Any deviation from normal was recorded with respect to time of onset, duration and intensity.

Statistics

Differences in relative ear oedema between the vehicle treated group and the other groups were tested for significance employing a non-parametric statistical method of analysis, the Mann-Whitney U test. The required level of significance was $p<0.05$.

All statistical analysis was performed employing the statistical software package Analyse-it v. 1.62.

Results

Clinical Signs

TPA caused an inflammation in the right ears, which was visible after about 30 minutes. It could clearly be observed that the right ears were bright red and the left ears pale. The test articles to some extent prevented the reaction in the right ear. No adverse reactions to Compound 51 or the groups treated with its components were observed.

Ear Oedema

The various concentrations of the test articles inhibited the relative oedema as shown in the table below:

| Drug | Dose | % Inhibition of relative ear oedema | Mann-Whitney U test |
|---|---|---|---|
| Vehicle | — | — | — |
| Niacinamide | 64.1 µmol/ear | 18 | p = 0.0952 |
| Rac-1-glyceryl-monocaprylate | 4.58 µmol/ear | 22 | P = 0.0526 |
| Compound 51 | 4.58 µmol/ear | 66 | P < 0.001 |
| Betamethasone 17-valerate | 0.02 mg/ear | 66 | P < 0.001 |

Conclusion

Compound 51 yielded a statistically significant and dose dependent inhibition of ear oedema comparable to the effect of betamethasone 17-valerate, which was applied at the maximal human clinical dose. This level of efficacy for compound 51 is convincing, since betamethasone 17-valerate is one of the strongest topical steroids on the market. Furthermore, the result indicates a significant synergistic effect of the complex of the invention, since the antiinflammatory effect was 65% higher than the additive effect of the individual active components of the complex. This finding is very surprising and explains how it is possible to obtain an antiinflammatory effect comparable to a strong steroid with substances that are virtually non-toxic and do not induce any of the damaging effects to the skin caused by corticosteroids like betamethasone 17-valerate.

Example 112

Investigation of two complexes according to the invention in a recognized pharmacodynamic model of sub-chronic inflammation.

Objective

The objective of this study was to assess the therapeutic value of the complexes of the invention in a very demanding pharmacodynamic model of dermal inflammation. Repeated application of TPA to the ears of the mice within 48 hours yields an inflammatory lesion with infiltration of leukocytes and persistent swelling. The reapplication of TPA (8 mg/ear) after 48 hours produces an inflammation and ear oedema, which is more dramatic due to the involvement and activation of a vast number of inflammatory cells. Therefore the model is suitable for drug evaluation in relation to more aggravated or chronic inflammatory conditions. The test substance for evaluation is co-applied with the second TPA application. Specifically, the inventor has observed that mild steroids like hydrocortisone have no effect in this model, while only strong steroids have a more significant effect, reflecting the requirements for success in the clinical situation (Stanley P L et al.: Mouse skin inflammation induced by multiple topical applications of 12-O-tetradecanoylphorbol-13-acetate. Skin Pharmacology 1991, 4: 262-71).

Test Articles and Vehicle

The test articles are the complexes prepared according to example 51 (Compound 51 in the following) and example 107 (Compound 107 in the following). All substances were obtained from Astion A/S, Denmark.

Animals

The study was performed in 80 female BALB/ca mice from M & B A/S, DK-8680 Ry. At start of the acclimatisation period the mice were in the weight range of 20 g (+/−5 g).

Housing

The study took place in an animal room provided with filtered air. The temperature in the room was set at 21-23° C. and the relative humidity to ≧30%. The room was illuminated to give a cycle of 12 hours light and 12 hours darkness. Light was on from 06.00 till 18.00 h.

The animals were housed in Macrolon type III cages (40× 25×14 cm), 10 in each cage. The cages were cleaned and the bedding changed at least once a week.

Bedding

The bedding was sawdust (Tapvei 4HV) from Tapvei Oy, 73620 Kortteinen, Finland.

Diet

A complete pelleted rodent diet "Altromin 1324" from Chr. Petersen, DK-4100 Ringsted, was available ad libitum.

Drinking Water

The animals had free access to bottles with domestic quality drinking water. The drinking water was changed daily.

Animal Randomisation and Allocation

On the day of arrival the animals were randomly allocated to groups of 10 mice.

Body Weight

The animals were weighed on the day of dosing and termination of the study.

Procedure

All groups were treated with 20 μl TPA solution 400 μg/ml in acetone, on the right ear. 48 hours later. The test substances were administered 20 minutes before and 20 minutes after re-application of TPA to the ear (20 μl TPA solution 400 μg/ml in acetone, on the right ear).

The groups (n=10) and doses were as follows:

| Group | Drug | Dose |
| --- | --- | --- |
| 1 | Vehicle | — |
| 2 | Compound 51 | 0.5 mg/ear |
| 3 | Compound 51 | 1.0 mg/ear |
| 4 | Compound 51 | 2.0 mg/ear |
| 5 | Compound 107 | 0.5 mg/ear |
| 6 | Compound 107 | 0.1 mg/ear |
| 7 | Compound 107 | 2.0 mg/ear |
| 8 | Betamethasone 17-valerate | 0.02 mg/ear |

Three hours after the TPA application the mice were sacrificed, the ears cut from the tip with a punch biopsy knife (8 mm diameter) and weighed.

Mean weights and standard deviations were calculated. Relative ear oedema was assessed as the weight difference between right and left ear of each mouse expressed as percent of the left ear. Percent inhibition of the relative ear oedema compared with the vehicle treated groups was calculated for the test substance and positive control treated group.

Clinical Signs

All visible signs of ill health and any behavioural changes were recorded daily during the study. Any deviation from normal was recorded with respect to time of onset, duration and intensity.

Statistics

Differences in relative ear oedema between the vehicle treated group and the other groups were tested for significance employing a non-parametric statistical method of analysis, the Mann-Whitney U test. The required level of significance was $p<0.05$.

All statistical analysis was performed employing the statistical software package Analyse-it v. 1.62.

Results

Clinical Signs

TPA caused an inflammation in the right ears, which was visible after about 30 minutes. It could clearly be observed that the right ears were bright red and the left ears pale. The test articles to some extent prevented the reaction in the right ear. No adverse reactions to Compound 51 or the groups treated with its components were observed.

Ear Oedema

The various concentrations of the test articles inhibited the relative oedema as shown in the table below:

| Drug | Dose | % Inhibition of relative ear oedema | Mann-Whitney U test |
| --- | --- | --- | --- |
| Vehicle | — | — | — |
| Compound 51 | 0.5 mg/ear | 21 | p = 0.0753 |
| Compound 51 | 1.0 mg/ear | 26 | p = 0.0219 |
| Compound 51 | 2.0 mg/ear | 27 | p = 0.0344 |
| Compound 107 | 0.5 mg/ear | 28 | p = 0.0159 |
| Compound 107 | 0.1 mg/ear | 30 | p = 0.0113 |
| Compound 107 | 2.0 mg/ear | 50 | P < 0.0001 |
| Betamethasone 17-valerate | 0.02 mg/ear | 31 | p = 0.0103 |

Conclusion

The study demonstrates a dose-dependent and statistically significant effect of both Compound 107 and Compound 51. In the two highest doses Compound 51 reaches a level of efficacy, which is statistically significant and comparable to that of betamethasone 17-valerate, only slightly lower. This is a very noteworthy finding since betamethasone 17-valerate is one of the strongest topical steroids on the market, which may only be used for short periods due to significant adverse effects, while Compound 51 is literally non-toxic and suitable for long-term daily skin treatment or skin care. The study also shows that Compound 107 is comparable to betamethasone 17-valerate at the two lowest doses, but statistically significantly stronger (p=0.0089, Mann-Whitney U test) than betamethasone 17-valerate at the highest dose, yielding over 60% more anti-inflammatory effect than the strong steroid. The results are clinically relevant since all of the tested doses of Compound 107 and Compound 51 may be applied clinically to humans, due to the favourable safety profile.

Example 113

Objective

The objective of this study was to assess the antimicrobial effect of a complex of the invention and the corresponding doses of its components in a number of pathogenic bacteria and fungi.

Test Articles and Vehicle

The test articles are the complex prepared according to example 51 (Compound 51 in the following) and its components Glyceryl-1-octanoate and niacinamide. All substances were obtained from Astion A/S, Denmark.

Experimental Procedure

Test substance or vehicle is added to test wells containing the selected microorganisms ($1 \times 10^4$ to $5 \times 10^5$ CFU/ml) in cultures grown under controlled conditions. The final innoculum concentration is determined by reference to a standard optical density curve and adjusted as required. After 1 to 4 days, growth of the culture is examined and scored positive (+) for inhibition of growth or turbidity, or negative (−) for no effect upon growth or turbidity. An initial test concentration of 3 mM in 1% DMSO is used and dilutions are tested to establish the minimal inhibitory concentration (MIC).

Results

The substances are administered so that the molar concentration of the complex is directly comparable to the molar concentration of the components of the complex. The following table shows the MIC obtained for each substance:

| Organism | Compound 51 | Glyceryl-1-octanoate | Niacinamide |
| --- | --- | --- | --- |
| Candida albicans | 300 µM | Not active at tested doses | Not active at tested doses |
| Epidermophyton floccosum | 1000 µM | Not active at tested doses | Not active at tested doses |
| Microsporum canis | 1000 µM | Not active at tested doses | Not active at tested doses |
| Streptococcus faecalis | 3 mM | Not active at tested doses | Not active at tested doses |
| Trichophyton rubrum | 1000 µM | Not active at tested doses | Not active at tested doses |

Conclusion

The data clearly show that the complexes of the invention are superior to the corresponding doses of their individual components, since the complexes displayed clear anti-fungal and anti-bacterial effects, while the components were without effect at the same doses. This clearly demonstrates a synergistic effect of the complex of the invention.

Example 114

Objective

The objective of this study was to assess the antibacterial effect of a complex of the invention against a mithicillin resistant bacteria strain.

Test Articles and Vehicle

The test articles are the complex prepared according to example 51 (Compound 51 in the following). All substances were obtained from Astion A/S, Denmark.

Experimental Procedure

Test substance or vehicle is added to test wells containing the selected microorganisms ($1 \times 10^4$ to $5 \times 10^5$ CFU/ml) in cultures grown under controlled conditions. The final innoculum concentration is determined by reference to a standard optical density curve and adjusted as required. After 1 to 4 days, growth of the culture is examined and scored positive (+) for inhibition of growth or turbidity, or negative (−) for no effect upon growth or turbidity. An initial test concentration of 3 mM in 1% DMSO is used and dilutions are tested to establish the minimal inhibitory concentration (MIC).

Results

The substances are administered so that the molar concentration of the complex is directly comparable to the molar concentration of the components of the complex. The following table shows the MIC obtained for each substance:

| Organism | Compound 51 |
| --- | --- |
| Staphylococcus aureus | 1000 µM |
| Staphylococcus aureus Methicillin Resistant | 300 µM |

Conclusion

The data clearly show that the complex of the invention has a convincing inhibiting effect on *Staphylococcus aureus*. Furthermore it is observed that complex is even more effective against the Mithicillin resistant strain, where many existing antibiotics typically show weaker activity against resistant strains.

Example 115

Four human subjects (all male) suffering from moderate to severe seborrhoeic dermatitis in the face were treated with the lotion produced in example 111 for four weeks. All had a stable disease at the start of treatment and had been suffering from the disease for several years.

One subject experienced a clear improvement of erythema and scaling within 4 days and had an almost cleared face after one week. After two weeks all symptoms were completely gone. Therefore the treatment was stopped and after one week the symptoms had started to come back. Treatment was reinitiated and after two days all symptoms had gone. The three other subjects had a very similar experience. They experienced gradual clear improvement during the first two weeks. After three weeks two stopped treatment because they were virtually symptom free. The last subject was symptom free after four weeks. The two that stopped after three weeks experienced no reoccurrence of symptoms after four weeks.

Example 116

Two human subjects suffering from moderate persistent acne were treated for 8 weeks with a gel with the following composition (w/w) %:

| Water: | Ad 100% |
| --- | --- |
| Complex: | 5.0% |

-continued

| | |
|---|---|
| Methylparabene: | 0.1% |
| Carbopol ETD 2020 (Noveon): | 0.8.0% |
| Potassium hydroxide 10% | ad pH 6.0 |
| Propylene glycol: | 2.0% |
| Glycerol: | 2.0% |

The complex used in this formulation was the one produced in example 51. One subject experienced a pronounced improvement during the first week of treatment. This continued and the subject was at least 80% improved after 4 weeks and remained stable until the end of the treatment. The other subject had a slow improvement the first three weeks. Thereafter the improvement was very significant over two weeks. The subject was completely free of symptoms the last three weeks of treatment.

The invention claimed is:

1. A composition for the treatment of dermal inflammation, comprising a combination of
   (i) glyceryl monocaprylate or an alkali metal salt thereof and
   (ii) niacinamide or a salt thereof,
   wherein the component (i) and the component (ii) are present in a molar ratio of between about 1:3 and 1:16.

2. The composition according to claim 1, wherein the component (i) is racemic, enantiomerically enriched or enantiomerically pure 1-glyceryl-monocaprylate and wherein component (ii) is niacinamide.

3. The composition according to claim 1, further comprising one or more excipient(s) or carrier(s) for the formulation of a pharmaceutical, or a cosmetic.

4. The composition according to claim 3, further comprising one or more therapeutically active agents.

5. The composition according to claim 3, formulated for topical, or transdermal administration.

6. The composition according to claim 5, formulated for topical administration.

7. The composition according to claim 2, wherein the 1-glyceryl monocaprylate and the niacinamide or a salt thereof, are present in a molar ratio of about 1:14 or about 2:7.

* * * * *